United States Patent
Monson et al.

(10) Patent No.: US 12,048,613 B2
(45) Date of Patent: Jul. 30, 2024

(54) INCONTINENCE DETECTION SYSTEM

(71) Applicant: Hill-Rom Services, Inc., Batesville, IN (US)

(72) Inventors: Gavin M. Monson, Oxford, OH (US); Jason M. Williams, Corydon, IN (US); Douglas A. Seim, Okeana, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 750 days.

(21) Appl. No.: 17/195,023

(22) Filed: Mar. 8, 2021

(65) Prior Publication Data

US 2021/0205151 A1    Jul. 8, 2021

Related U.S. Application Data

(63) Continuation-in-part of application No. 17/027,881, filed on Sep. 22, 2020, now Pat. No. 11,712,186.

(60) Provisional application No. 62/908,001, filed on Sep. 30, 2019.

(51) Int. Cl.
*A61F 13/42* (2006.01)
*A61F 13/15* (2006.01)
*A61F 13/84* (2006.01)
*G08B 7/06* (2006.01)
*H04W 84/12* (2009.01)

(52) U.S. Cl.
CPC .... *A61F 13/42* (2013.01); *A61F 2013/15121* (2013.01); *A61F 2013/424* (2013.01); *A61F 2013/8482* (2013.01); *G08B 7/06* (2013.01); *H04W 84/12* (2013.01)

(58) Field of Classification Search
CPC ............ A61F 13/42; A61F 2013/15121; A61F 2013/424; A61F 2013/8482; G08B 7/06; G08B 21/00–21/0211; H04W 84/12
See application file for complete search history.

(56) References Cited

U.S. PATENT DOCUMENTS

| 1,772,232 A | 8/1930 | Guilder |
| 2,127,538 A | 8/1938 | Seiger |
| 2,644,050 A | 6/1953 | Seiger |
| 2,668,202 A | 2/1954 | Kaplan |
| 2,726,294 A | 12/1955 | Kroening et al. |

(Continued)

FOREIGN PATENT DOCUMENTS

| CA | 2361145 | 12/1999 |
| CA | 2494896 | 12/1999 |

(Continued)

OTHER PUBLICATIONS

Communication pursuant to Article 94(3) EPC issued by the European Patent Office in European Patent Application No. 20198656.9; dated Jul. 26, 2023; 8 pages.

*Primary Examiner* — Jonathan T Kuo
(74) *Attorney, Agent, or Firm* — Barnes & Thornburg LLP

(57) ABSTRACT

A patient support apparatus includes a frame and a mattress supported by the frame and arranged to support a patient thereon. A sensor is included to detect moisture on the patient and/or the patient support apparatus. The sensor produces signals indicative of the presence of moisture on the patient support apparatus. One or more alerts are output in response to the signals provided by the sensor to notify a caregiver of the presence of moisture on the patient support apparatus.

17 Claims, 16 Drawing Sheets

(56) References Cited

U.S. PATENT DOCUMENTS

| | | | |
|---|---|---|---|
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,539,559 A | 9/1985 | Kelley et al. |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibelin |
| 5,760,694 A | 6/1998 | Nissim et al. |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 5,949,332 A | 9/1999 | Kim |
| 6,028,241 A | 2/2000 | Armstead |
| 6,047,419 A | 4/2000 | Fergusaon |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,774,800 B2 | 8/2004 | Friedman et al. |
| 6,831,562 B2 | 12/2004 | Rodgers et al. |
| 6,832,507 B1 | 12/2004 | Berg et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,471,706 B2 * | 6/2013 | Schuster ............... G06Q 10/08 340/572.1 |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 9,048,819 B2 | 6/2015 | Rokhsaz et al. |
| 9,107,776 B2 | 8/2015 | Bergman et al. |
| 9,135,478 B2 * | 9/2015 | Burns .............. G06K 19/07743 |
| 9,904,885 B2 * | 2/2018 | Sengstaken, Jr. ......... A61J 7/04 |
| 10,115,291 B2 | 10/2018 | Tallent et al. |
| 11,712,186 B2 * | 8/2023 | Monson ............... A61B 5/0022 600/300 |
| 2002/0002633 A1 | 1/2002 | Colling, III |
| 2002/0011932 A1 | 1/2002 | Rodgers et al. |
| 2002/0033757 A1 | 3/2002 | Rodgers et al. |
| 2002/0145526 A1 | 10/2002 | Friedman et al. |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0052282 A1 | 3/2005 | Rodgers et al. |
| 2005/0060246 A1 | 3/2005 | Lastinger et al. |
| 2005/0099294 A1 | 5/2005 | Bogner et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |

(56) References Cited

U.S. PATENT DOCUMENTS

| | | |
|---|---|---|
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0208886 A1 | 9/2006 | Beamer |
| 2006/0270351 A1 | 11/2006 | Lastinger et al. |
| 2006/0279427 A1 | 12/2006 | Becker et al. |
| 2007/0159332 A1* | 7/2007 | Koblasz ............... A61B 5/411 340/572.1 |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2010/0060452 A1* | 3/2010 | Schuster ............... G06Q 10/08 340/572.1 |
| 2010/0072271 A1 | 3/2010 | Thorstensson |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 | 12/2011 | Bunza et al. |
| 2012/0092027 A1 | 4/2012 | Forster |
| 2012/0119912 A1 | 5/2012 | Ortega et al. |
| 2012/0119915 A1 | 5/2012 | Clement et al. |
| 2012/0130330 A1 | 5/2012 | Wilson et al. |
| 2012/0165772 A1 | 6/2012 | Groosman et al. |
| 2012/0217311 A1 | 8/2012 | Rokhsaz et al. |
| 2012/0268278 A1 | 10/2012 | Lewis et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0189946 A1 | 7/2013 | Swanson |
| 2013/0233924 A1* | 9/2013 | Burns ................ G06K 7/0021 235/441 |
| 2013/0254141 A1 | 9/2013 | Barda et al. |
| 2014/0070950 A1 | 3/2014 | Snodgrass |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0296808 A1 | 10/2014 | Curran et al. |
| 2014/0358099 A1 | 12/2014 | Durgin et al. |
| 2015/0076221 A1 | 3/2015 | Rushing |
| 2015/0080819 A1 | 3/2015 | Charna et al. |
| 2015/0080834 A1 | 3/2015 | Mills |
| 2015/0087935 A1 | 3/2015 | Davis et al. |
| 2015/0164438 A1 | 6/2015 | Halperin et al. |
| 2015/0286852 A1* | 10/2015 | Sengstaken, Jr. ......... A61J 7/04 340/10.1 |
| 2016/0089059 A1* | 3/2016 | Hu ................ A61B 5/7207 600/595 |
| 2016/0157755 A1 | 6/2016 | Becker et al. |
| 2017/0065464 A1 | 3/2017 | Heil et al. |
| 2017/0098044 A1 | 4/2017 | Lai et al. |
| 2017/0309115 A1 | 10/2017 | Tallent et al. |
| 2018/0021184 A1* | 1/2018 | Monson ............... H01Q 9/0457 340/573.5 |
| 2021/0275773 A1* | 9/2021 | Albala ................. H05B 47/12 |

FOREIGN PATENT DOCUMENTS

| | | |
|---|---|---|
| CN | 102568259 | 7/2012 |
| CN | 202711437 | 1/2013 |
| CN | 102985853 | 3/2013 |
| DE | 4137631 | 5/1992 |
| DE | 69906388 | 2/2004 |
| DE | 69915370 | 3/2005 |
| DE | 69917491 | 5/2005 |
| DE | 60016946 | 6/2006 |
| DE | 102007050074 | 4/2009 |
| EP | 0335279 | 10/1989 |
| EP | 1147603 | 10/2001 |
| EP | 1149305 | 10/2001 |
| EP | 1153317 | 11/2001 |
| EP | 1218771 | 7/2002 |
| EP | 1286179 | 2/2003 |
| EP | 1153317 | 3/2003 |
| EP | 1147603 | 3/2004 |
| EP | 1410353 | 4/2004 |
| EP | 1149305 | 5/2004 |
| EP | 1218771 | 12/2004 |
| EP | 1684615 | 8/2006 |
| EP | 1868553 | 12/2007 |
| EP | 1897278 | 3/2008 |
| EP | 1959900 | 8/2008 |
| EP | 1994650 | 11/2008 |
| EP | 2014267 | 1/2009 |
| EP | 1410353 | 12/2009 |
| EP | 1897278 | 1/2010 |
| EP | 1684615 | 2/2010 |
| EP | 2156222 | 2/2010 |
| EP | 2313044 | 4/2011 |
| EP | 1959900 | 2/2012 |
| EP | 2444039 | 4/2012 |
| EP | 2452183 | 5/2012 |
| EP | 2496197 | 9/2012 |
| EP | 1994650 | 12/2012 |
| EP | 2542200 | 1/2013 |
| EP | 2579069 | 4/2013 |
| EP | 2582341 | 4/2013 |
| EP | 2729107 | 5/2014 |
| EP | 2738748 | 6/2014 |
| EP | 2739254 | 6/2014 |
| EP | 2156222 | 8/2015 |
| EP | 2019659 | 4/2016 |
| EP | 2739254 | 11/2016 |
| GB | 145859 | 3/1919 |
| GB | 2145859 | 4/1985 |
| GB | 2408204 | 11/2003 |
| WO | WO 89/10110 | 4/1989 |
| WO | WO 94/20002 | 3/1994 |
| WO | WO 00/44091 | 7/2000 |
| WO | WO 01/25817 | 4/2001 |
| WO | WO 01/85085 | 11/2001 |
| WO | WO 02/103645 | 12/2002 |
| WO | WO 2006/108540 | 10/2006 |
| WO | WO 2007/069968 | 6/2007 |
| WO | WO 2008/130298 | 10/2008 |
| WO | WO 2010/001271 | 1/2010 |
| WO | WO 2010/043368 | 4/2010 |
| WO | WO 2011/107580 | 9/2011 |
| WO | WO 2012/136157 | 10/2012 |
| WO | WO 2014/165041 | 10/2014 |
| WO | WO 2015/137999 | 9/2015 |
| WO | 2019036155 A1 | 2/2019 |

\* cited by examiner

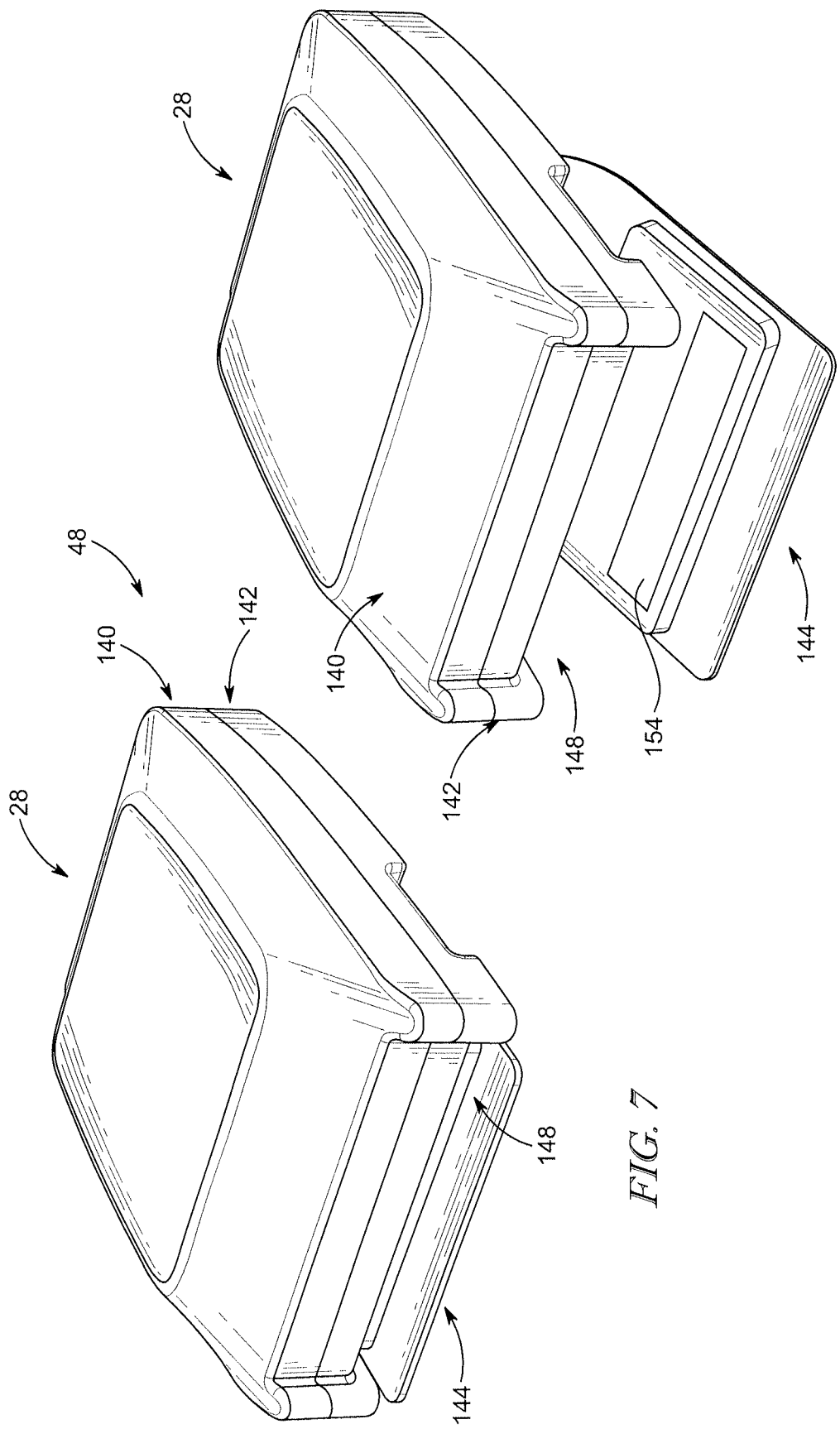

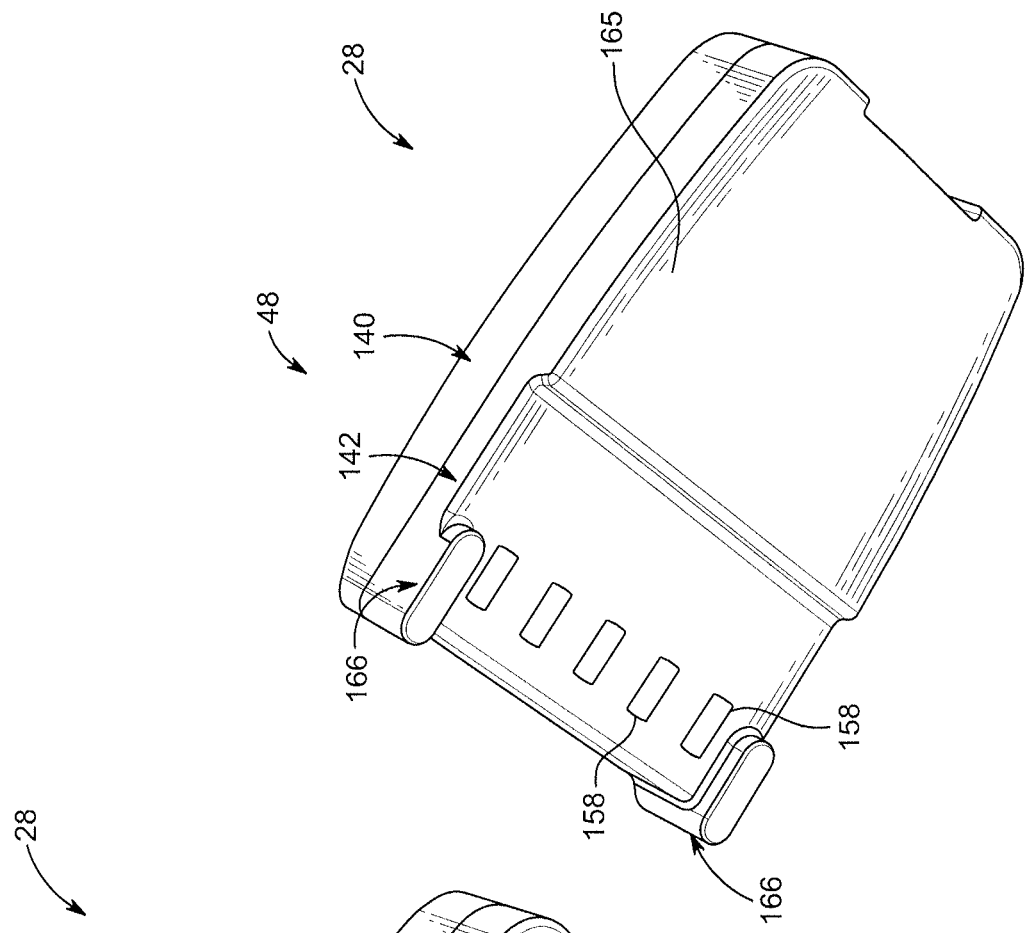
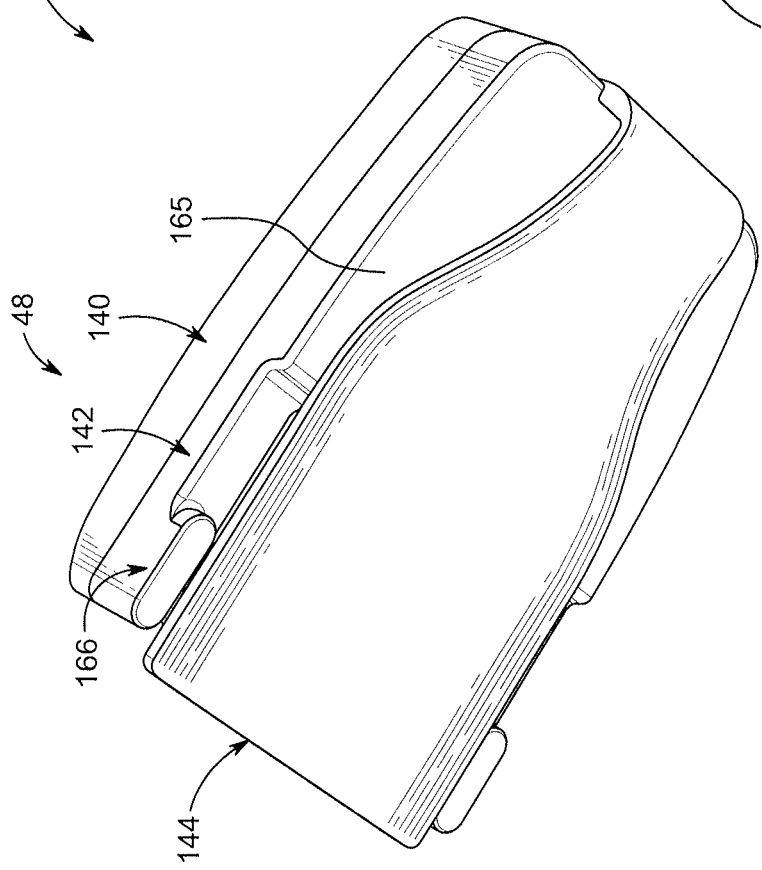
FIG. 11
FIG. 10

INCONTINENCE DETECTION SYSTEM

PRIORITY CLAIM

This application is a continuation-in-part of U.S. application Ser. No. 17/027,881, filed Sep. 22, 2020, and claims priority under 35 U.S.C. § 119(e) to U.S. Provisional Application Ser. No. 62/908,001, filed Sep. 30, 2019, each of which is expressly incorporated by reference herein.

BACKGROUND

The present disclosure relates to patient support apparatuses having alerting capabilities. More specifically, the present disclosure relates to patient support apparatuses that include sensors for monitoring an incontinence state of a patient and structures for alerting caregivers when moisture is detected.

Patients in healthcare facilities may become incontinent and may need the wetness to be removed from the bed to prevent undesirable side effects. In some situations, moisture is detected by an incontinence detection system but a location of the patient may not immediately be known. Furthermore, other persons in the vicinity of the patient and the hospital bed may become upset if they notice an alert that the patient has become incontinent yet no caregivers are available to immediately assist them.

Locating systems are used in various facilities to determine the whereabouts of people and equipment. Such locating systems are used widely in healthcare facilities, for example, to determine the locations of caregivers and medical equipment. A variety of wireless technologies such as infrared (IR), radio frequency (RF), ultrasound, and so forth have been used for communication between locating tags and receivers or transceivers. In recent times, ultra-wideband (UWB) locating systems have been developed and are able to determine the locations of locating tags much more accurately than the predecessor systems.

While UWB locating systems are known in general, the industry has not yet fully realized the potential for more sophisticated algorithms in connection with such locating systems. Accordingly, a need persists for improvements in high-accuracy locating systems, such as UWB locating systems, particularly those used in healthcare facilities.

SUMMARY

The present application discloses one or more of the features recited in the appended claims and/or the following features which, alone or in any combination, may comprise patentable subject matter:

In a first aspect of the present disclosure, a system for detecting and locating an incontinence event includes a patient support apparatus configured to support a patient thereon. The system may further include an incontinence detection pad including a condition-responsive sensor configured to provide incontinence signals indicative of incontinence data. The system may further include an ultra-wideband communications system coupled communicatively with the incontinence detection pad and configured to provide a transmission of data signals including: (i) incontinence signals indicative of the incontinence data sensed by the condition responsive sensor and (ii) location signals indicative of location data of the incontinence detention pad and the patient support apparatus.

In some embodiments of the first aspect, the ultra-wideband communication system includes an ultra-wideband tag coupled with the condition responsive sensor. The ultra-wideband communication system may further include an ultra-wideband reader coupled communicatively with the ultra-wideband tag. The ultra-wideband communication system may further include a controller including a microprocessor and a memory storage device storing instructions that when executed by the microprocessor cause the controller to output a command signal to notify a caregiver of the incontinence data and the location data of the incontinence detention pad and the patient support apparatus.

In some embodiments of the first aspect, the condition responsive sensor includes a detection grid configured to sense the presence of moisture and an radio-frequency identification tag configured to provide an input signal to the ultra-wideband tag.

In some embodiments of the first aspect, the ultra-wideband tag is configured to provide signals to the ultra-wideband reader based on the input signal and the controller is configured to determine a location and an incontinence state of the incontinence detection pad based on the signals provided by the ultra-wideband tag.

In some embodiments of the first aspect, the ultra-wideband reader and the ultra-wideband tag provide a low-power, high-accuracy location system and the controller is configured to determine the location of the incontinence detection pad based on the signals provided by the ultra-wideband tag with an accuracy within about a foot of the ultra-wideband tag.

In some embodiments of the first aspect, the radio frequency identification tag includes a distinct flap coupled to the patient support apparatus and the distinct flap hangs down below a surface of the patient support apparatus.

In some embodiments of the first aspect, the radio frequency identification tag is included in the incontinence detection pad and the incontinence detection pad has an outer dimension that is greater than a corresponding outer dimension of the patient support apparatus so that the ultra-wideband tag hangs below a surface of the patient support apparatus unobstructed from the patient supported by the patient support apparatus.

In some embodiments of the first aspect, the condition-responsive sensor includes a detection grid with a plurality of traces extending through a substrate and an ohmic sensor configured to measure a resistance between at least two of the plurality of traces and the ultra-wideband reader is coupled with the ohmic sensor.

In some embodiments of the first aspect, the ohmic sensor is configured to provide incontinence signals to the ultra-wideband reader indicative of the resistance between the at least two traces and the controller is configured to determine if moisture is present on the incontinence detention pad based on the signals provided by the ohmic sensor through the ultra-wideband reader.

In some embodiments of the first aspect, the ohmic sensor includes a microprocessor and a memory device storing instructions that, when executed, cause the ohmic sensor to change from a sleep mode, in which the ohmic sensor provides no signals to the ultra-wideband reader, and an active mode, in which the ohmic sensor is awake and provides the incontinence signals to the ultra-wideband reader.

In some embodiments of the first aspect, the memory device stores instructions that, when executed, cause the ohmic sensor to change from the sleep mode to the active mode about twice every minute.

In some embodiments of the first aspect, the ultra-wideband tag includes a battery and the ultra-wideband tag is configured to provide battery signals indicative of a charge state of the battery and the controller is configured to determine a useful life of the battery simultaneously with the incontinence signals and the location signals and output a command signal to cause a notification when the charge state of the battery reaches a predetermined threshold.

In some embodiments of the first aspect, the battery is configured to be recharged when the controller determines that the charge state of the battery has reached the predetermined threshold.

In some embodiments of the first aspect, the battery is recharged wirelessly when the controller determines that the charge state of the battery has reached the predetermined threshold.

In some embodiments of the first aspect, the ultra-wideband communication system is configured to relay the incontinence data and the location data to a network for incorporation into a patient's electronic medical record.

According to a second aspect of the present disclosure, a method includes providing an incontinence detection pad. The method may further include sensing for an incontinence event on the patient support apparatus. The method may further include outputting a first signal indicative of incontinence data. The method may further include outputting a second signal indicative of location data of the patient support apparatus.

In some embodiments of the second aspect, the first signal and the second signal are output simultaneously over an ultra-wideband communication system.

In some embodiments of the second aspect, the ultra-wideband communication system includes an ultra-wideband tag, an ultra-wideband reader coupled communicatively with the incontinence detection pad, and a controller and the method further comprises receiving the first and second signals with the ultra-wideband reader, determining if an incontinence event has occurred with the controller and, if the incontinence event has occurred, outputting a command signal from the controller to notify a caregiver of the location data of the incontinence detention pad and the patient support apparatus.

In some embodiments of the second aspect, the condition responsive sensor includes a detection grid configured to sense the presence of moisture and an radio-frequency identification tag configured to provide an input signal to the ultra-wideband tag.

In some embodiments of the second aspect, the ultra-wideband tag is configured to provide intermediate pulses of signals that are received by the ultra-wideband reader and the controller is configured to determine a location and an incontinence state of the incontinence detection pad based on the signals provided by the ultra-wideband tag.

In some embodiments of the second aspect, the ultra-wideband reader and the ultra-wideband tag provide a low-power, high-accuracy location system and the controller is configured to determine the location of the incontinence detection pad based on the signals provided by the ultra-wideband tag with an accuracy within about a foot of the ultra-wideband tag.

In some embodiments of the second aspect, the step of sensing for the incontinence event includes sensing for the incontinence event with a condition-responsive sensor that includes a detection grid with a plurality of traces extending through a substrate and an ohmic sensor configured to measure a resistance between at least two of the plurality of traces.

In some embodiments of the second aspect, the ohmic sensor is configured to provide incontinence signals indicative of the resistance between the at least two traces and the method further comprises determining if moisture is present on the incontinence detention pad based on the signals provided by the ohmic sensor.

In some embodiments of the second aspect, the ohmic sensor includes a microprocessor and a memory device storing instructions that, when executed, cause the ohmic sensor to change from a sleep mode, in which the ohmic sensor provides no signals to the ultra-wideband reader, and an active mode, in which the ohmic sensor is awake and provides the incontinence signals to the ultra-wideband reader.

In some embodiments of the second aspect, the memory device stores instructions that, when executed, cause the ohmic sensor to change from the sleep mode to the active mode about twice every minute.

In some embodiments of the second aspect, the ultra-wideband tag further includes a battery and the ultra-wideband tag is configured to provide battery signals indicative of a charge state of the battery and the controller is configured to determine a useful life of the battery simultaneously with the first signal and the second signal and output a command signal to cause a notification when the charge state of the battery reaches a predetermined threshold.

In some embodiments of the second aspect, the battery is configured to be recharged when the controller determines that the charge state of the battery has reached the predetermined threshold.

In some embodiments of the second aspect, the battery is recharged wirelessly when the controller determines that the charge state of the battery has reached the predetermined threshold.

In some embodiments of the second aspect, the step of outputting the command signal includes relaying the incontinence data and the location data to a network for incorporation in a patient's electronic medical record.

In some embodiments of the second aspect, the method further comprises a step of outputting a third signal indicative of patient data through the ultra-wideband communication system simultaneously with the first signal and the second signal.

According to a third aspect of the present disclosure, a system for detecting and locating an incontinence event includes a patient support apparatus configured to support a patient thereon. The system may further include an incontinence detection pad including a condition-responsive sensor configured to provide signals indicative of incontinence data. The system may further include a diagnostic patch configured to provide signals indicative of patient data. The system may further include an ultra-wideband communications system coupled communicatively with the incontinence detection pad and the diagnostic patch and configured to simultaneously provide signals indicative of the incontinence data sensed by the condition responsive sensor, the patient data sensed by the diagnostic patch, and location data of the incontinence detention pad and the patient support apparatus.

In some embodiments of the third aspect, the ultra-wideband communication system includes an ultra-wideband tag, an ultra-wideband reader coupled communicatively with the incontinence detection pad, and a controller including a microprocessor and a memory storage device storing instructions that when executed by the microprocessor cause the controller to output a command signal to notify a caregiver of the incontinence data, the location data of the incontinence detention pad and the patient support apparatus, and the patient data.

In some embodiments of the third aspect, the condition responsive sensor includes a detection grid configured to sense the presence of moisture and an radio-frequency identification tag configured to provide an input signal to the ultra-wideband tag.

In some embodiments of the third aspect, the ultra-wideband tag is configured to provide intermediate pulses of signals that are received by the ultra-wideband reader and the controller is configured to determine a location of the incontinence detection pad based on the signals provided by the ultra-wideband tag.

In some embodiments of the third aspect, the ultra-wideband reader and the ultra-wideband tag provide a low-power, high-accuracy location system and the controller is configured to determine the location of the incontinence detection pad based on the signals provided by the ultra-wideband tag with an accuracy within about a foot of the ultra-wideband tag.

In some embodiments of the third aspect, the radio frequency identification tag includes a distinct flap coupled to the patient support apparatus and the distinct flap hangs down below a plane of the patient support apparatus.

In some embodiments of the third aspect, the radio frequency identification tag is included in the incontinence detection pad and the incontinence detection pad has an outer dimension that is greater than a corresponding outer dimension of the patient support apparatus so that the ultra-wideband tag hangs below a plane of the patient support apparatus unobstructed from the patient supported by the patient support apparatus.

In some embodiments of the third aspect, the condition-responsive sensor includes a detection grid with a plurality of traces extending through a substrate and an ohmic sensor configured to measure a resistance between at least two of the plurality of traces and the ultra-wideband reader is coupled with the ohmic sensor.

In some embodiments of the third aspect, the ohmic sensor is configured to provide incontinence signals to the ultra-wideband reader indicative of the resistance between the at least two traces and the controller is configured to determine if moisture is present on the incontinence detention pad based on the signals provided by the ohmic sensor through the ultra-wideband reader.

In some embodiments of the third aspect, the ohmic sensor includes a microprocessor and a memory device storing instructions that, when executed, cause the ohmic sensor to change from a sleep mode, in which the ohmic sensor provides no signals to the ultra-wideband reader, and an active mode, in which the ohmic sensor is awake and provides the incontinence signals to the ultra-wideband reader.

In some embodiments of the third aspect, the memory device stores instructions that, when executed, cause the ohmic sensor to change from the sleep mode to the active mode about twice every minute.

In some embodiments of the third aspect, the ultra-wideband tag includes a battery and the ultra-wideband tag is configured to provide battery signals indicative of a charge state of the battery and the controller is configured to determine a useful life of the battery simultaneously with the incontinence signals and the location signals and output a command signal to cause a notification when the charge state of the battery reaches a predetermined threshold.

In some embodiments of the third aspect, the battery is configured to be recharged when the controller determines that the charge state of the battery has reached the predetermined threshold.

In some embodiments of the third aspect, the battery is recharged wirelessly when the controller determines that the charge state of the battery has reached the predetermined threshold.

In some embodiments of the third aspect, the ultra-wideband communication system is configured to relay the incontinence data and the location data to a network for incorporation into a patient's electronic medical record.

According to a fourth aspect of the present disclosure an incontinence detection and location system includes an ultra-wideband communications system configured to be communicatively coupled with an incontinence detection pad having a condition-responsive sensor and simultaneously provide signals indicative of the incontinence data sensed by the condition responsive sensor and location data of the incontinence detention pad.

In some embodiments of the fourth aspect, the ultra-wideband communication system includes an ultra-wideband tag, an ultra-wideband reader coupled communicatively with the incontinence detection pad, and a controller including a microprocessor and a memory storage device storing instructions that when executed by the microprocessor cause the controller to output a command signal to notify a caregiver of location data of the incontinence detention pad and a status of the incontinence detection pad.

In some embodiments of the fourth aspect, the condition responsive sensor includes a detection grid configured to sense the presence of moisture and an radio-frequency identification tag configured to provide an input signal to the ultra-wideband tag.

In some embodiments of the fourth aspect, the ultra-wideband tag is configured to provide intermediate pulses of signals indicative of the input signal that are received by the ultra-wideband reader and the controller is configured to determine a location and incontinence state of the incontinence detection pad based on the signals provided by the ultra-wideband tag.

In some embodiments of the fourth aspect, the ultra-wideband reader and the ultra-wideband tag provide a low-power, high-accuracy location system and the controller is configured to determine the location of the incontinence detection pad based on the signals provided by the ultra-wideband tag with an accuracy within about a foot of the ultra-wideband tag.

In some embodiments of the fourth aspect, the condition-responsive sensor includes a detection grid with a plurality of traces extending through a substrate and an ohmic sensor configured to measure a resistance between at least two of the plurality of traces and the ultra-wideband reader is coupled with the ohmic sensor.

In some embodiments of the fourth aspect, the ohmic sensor is configured to provide incontinence signals to the ultra-wideband reader indicative of the resistance between the at least two traces and the controller is configured to determine if moisture is present on the incontinence detention pad based on the signals provided by the ohmic sensor through the ultra-wideband reader.

In some embodiments of the fourth aspect, the ohmic sensor includes a microprocessor and a memory device storing instructions that, when executed, cause the ohmic sensor to change from a sleep mode, in which the ohmic sensor provides no signals to the ultra-wideband reader, and an active mode, in which the ohmic sensor is awake and provides the incontinence signals to the ultra-wideband reader.

In some embodiments of the fourth aspect, the memory device stores instructions that, when executed, cause the ohmic sensor to change from the sleep mode to the active mode about twice every minute.

In some embodiments of the fourth aspect, the ultra-wideband tag includes a battery and the ultra-wideband tag is configured to provide battery signals indicative of a charge state of the battery and the controller is configured to determine a useful life of the battery simultaneously with the incontinence signals and the location signals and output a command signal to cause a notification when the charge state of the battery reaches a predetermined threshold.

In some embodiments of the fourth aspect, the battery is configured to be recharged when the controller determines that the charge state of the battery has reached the predetermined threshold.

In some embodiments of the fourth aspect, the battery is recharged wirelessly when the controller determines that the charge state of the battery has reached the predetermined threshold.

In some embodiments of the fourth aspect, the ultra-wideband communication system is configured to relay the incontinence data and the location data to a network for incorporation into a patient's electronic medical record.

In accordance with a fifth aspect of the present disclosure, a system for detecting an incontinence event includes a patient support apparatus configured to support a patient thereon. The system further includes an incontinence detection pad including a substrate and an incontinence detection grid coupled to the substrate and a communications system.

In some embodiments of the fifth aspect, the communications system includes a wireless tag coupled removably to the incontinence detection pad and configured to sense one or more electrical characteristics of the detection grid. The communications system may further include a wireless module coupled to the patient support apparatus and having an antenna to receive signals from the wireless tag including the one or more electrical characteristics sensed by the wireless tag, and circuitry coupled to the patient support apparatus configured to provide a transmission of data signals to a nurse call station including incontinence signals indicative of the occurrence of an incontinence event based on the one or more electrical characteristics.

In some embodiments of the fifth aspect, the circuitry includes a microprocessor and memory storing instructions that, when executed by the microprocessor, determines whether the incontinence event has occurred from the one or more electrical characteristics sensed by the wireless tag.

In some embodiments of the fifth aspect, the circuitry further includes a relay that is coupled to the nurse call station by a wired connection including a first connector coupled to the patient support apparatus and a second connector coupled to a wall located in a room where the patient support apparatus is located.

In some embodiments of the fifth aspect, the circuitry further includes a Wifi module coupled to the patient support apparatus and a wireless access point spaced apart from the patient support apparatus, and wherein the Wifi module is configured to wirelessly relay the data signals to the wireless access point and the wireless access point is communicatively coupled to the nurse call station.

In some embodiments of the fifth aspect, the wireless tag is configured to sense a first resistance of the one or more electrical characteristics of the detection grid at a first point in time and is configured to sense a second resistance of the one or more electrical characteristics of the detection grid at a second point in time, and wherein the circuitry is configured to compare the first resistance to the second resistance and provide incontinence signals indicating that the incontinence event has occurred only when a rate of change of the resistance of the detection grid exceeds a predetermined rate of change.

In some embodiments of the fifth aspect, the wireless tag includes a microprocessor and memory storing instructions that, when executed by the microprocessor, determines whether the incontinence event has occurred from the one or more electrical characteristics sensed by the wireless tag.

In some embodiments of the fifth aspect, the wireless tag is configured to determine a first resistance of the one or more electrical characteristics of the detection grid at a first point in time and is configured to determine a second resistance of the one or more electrical characteristics of the detection grid at a second point in time, and wherein the wireless tag is configured to compare the first resistance to the second resistance and provide incontinence signals indicating that the incontinence event has occurred only when a rate of change of the resistance of the detection grid exceeds a predetermined rate of change.

In some embodiments of the fifth aspect, the wireless tag includes a housing having an upper shell, a lower shell, and an attachment lever coupled to at least one of the upper shell and the lower shell, and wherein the attachment lever is moveable between an opened position in which the attachment lever is at least partially spaced from the lower shell, and a closed position, in which the attachment lever provides a compressive force on the incontinence detection pad.

In some embodiments of the fifth aspect, the attachment lever includes a flexible flange such that the attachment lever is configured to deform relative to the lower shell from the closed position to the opened position and is normally biased toward the closed position.

In some embodiments of the fifth aspect, the attachment lever includes a flange, an attachment rib coupled to the flexible flange and arranged to extend toward the lower shell, and an attachment magnet coupled to the attachment rib.

In some embodiments of the fifth aspect, the wireless tag includes a pair of index tabs and the incontinence detection pad is formed to include a pair of index openings that each receive one of the index tabs to position the wireless tag in contact with a plurality of conductive traces included in the detection grid.

In some embodiments of the fifth aspect, the wireless tag further includes a plurality of conductive contacts that are aligned with the attachment magnet and that are spaced apart laterally from one another, each conductive contact of the plurality of conductive contacts being arranged to engage a respective conductive contact of the plurality of conductive traces.

In some embodiments of the fifth aspect, the wireless tag includes an indicator light configured to display a first color and a second color different than the first color, the first color being displayed prior to the incontinence event, the second color being displayed after the incontinence event.

In some embodiments of the fifth aspect, the wireless tag includes an indicator light configured to display a first color and a second color different than the first color, he first color being displayed when the wireless tag has a power level above a predetermined amount, the second color being displayed when the wireless tag has a power level below the predetermined amount to indicate that a power source of the wireless tag should be recharged or replaced.

In some embodiments of the fifth aspect, the incontinence detection pad includes a distinct flap and the wireless tag is coupled to the distinct flap.

In some embodiments of the fifth aspect, the wireless tag is a clip-on tag and includes a housing, a power source located within an interior space defined by the housing, and circuitry located within the interior space defined by the housing, and wherein the housing is leak-tight so that the wireless tag is waterproof.

In some embodiments of the fifth aspect, the incontinence detection grid includes a plurality of conductive traces, the plurality of conductive traces including a peripheral loop and a pair of interior detection branches.

In some embodiments of the fifth aspect, the peripheral detection loop surrounds the interior detection branches and includes an inner trace and an outer trace spaced apart from the inner trace.

In some embodiments of the fifth aspect, each interior detection branch includes an arm and a plurality of fingers extending from the arm and each of the plurality of fingers extends toward the opposite arm that the plurality of fingers are connected to.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 7 is a perspective view of a clip-on wireless tag in a closed position in accordance with the present disclosure;

FIG. 8 is a perspective view of the wireless tag in an opened position;

FIG. 10 is another perspective view of the wireless tag;

FIG. 11 is a perspective view similar to FIG. 10 with a portion of the wireless tag removed to show a plurality of conductive contacts;

DETAILED DESCRIPTION

Figure 1:
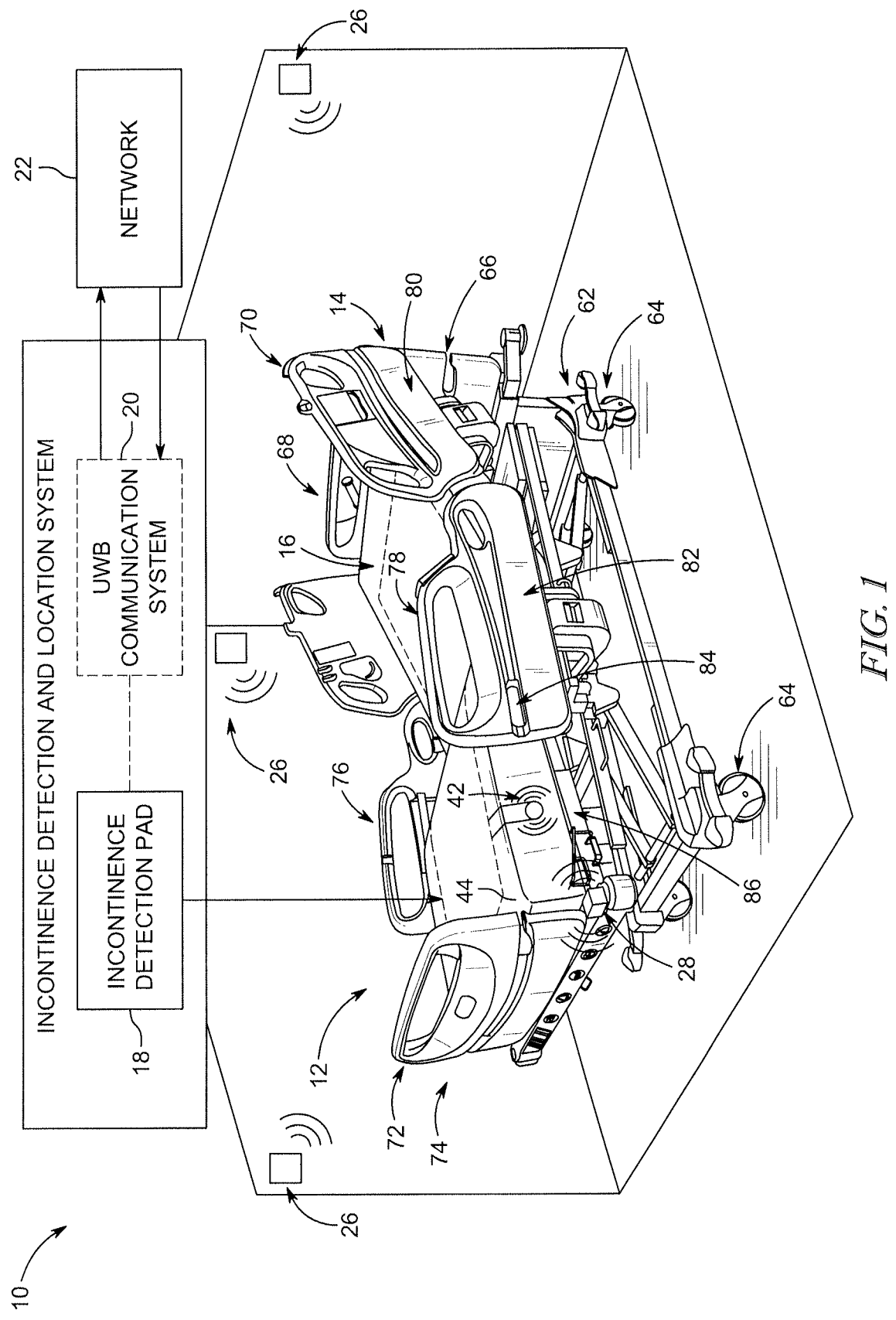
FIG. 1 is a perspective view of a patient support apparatus and an incontinence detection and notification system according to the present disclosure.

Referring to FIG. 1, a patient support apparatus 12 is illustratively embodied as a hospital bed. In some embodiments, the patient support apparatus may include a stretcher, cot, operating table, support table, patient recliner, chair, wheelchair, or other structures used to support a patient. The patient support apparatus 12 in the illustrative embodiment is located in a healthcare facility. In other embodiments, the patient support apparatus may be located in a remote location such as the patient's home or another acute care environment outside of a healthcare facility. The patient support apparatus 12 includes a frame 14, a mattress 16 supported on the frame 14. An example of a suitable frame 14 and mattress 16 is shown and described in U.S. Patent Pub. No. 2018/0184984 which is expressly incorporated by reference herein for the purpose of describing a suitable patient support apparatus with a frame and mattress along with associated functions and capabilities of the frame and mattress.

An incontinence detection and location system 10 is coupled to the patient support apparatus 12 and is configured to determine an incontinence state of a patient supported on the patient support apparatus. In the illustrative embodiment the term "incontinence" as used herein is intended to cover all biofluids such as blood, urine, fecal matter, interstitial fluid, saline, or any other fluid having a large concentration of ions that easily conduct electricity.

The incontinence detection and location system 10 includes an incontinence detection pad 18 and an ultra-wideband (UWB) communication system 20 as shown in FIG. 1. The incontinence detection pad 18 is coupled with the mattress 16 in the illustrative embodiment. In other embodiments, the incontinence detection pad 16 may be coupled to the frame 14 or may be coupled to one or more intervening structures between the mattress 16 and the incontinence detection pad 16. The UWB communication system 20 is communicatively coupled to the incontinence detection pad 18 and is configured to transfer data between the incontinence detection pad 18 and/or the patient support apparatus 12 and a network 22.

The incontinence detection pad 18 is positioned on the hospital bed 10, as suggested in FIG. 1, for surveillance for unwanted incontinence fluids or other biofluids that may be produced by a patient. The incontinence detection pad 18 may be removed and replaced without replacing the entire mattress 16 if the patient experiences an incontinence event. An example of a suitable incontinence detection pad with a condition-responsive sensor is shown and described in U.S. Patent Pub. Nos. 2017/0065464, U.S. Patent Pub. No. 2018/0021184, and U.S. Patent Pub. No. 2019/0060137, each of which is expressly incorporated by reference herein for the purpose of describing a suitable incontinence detection pad with one or more sensors for determining the incontinence status of the incontinence detection pad 18.

Figure 2:
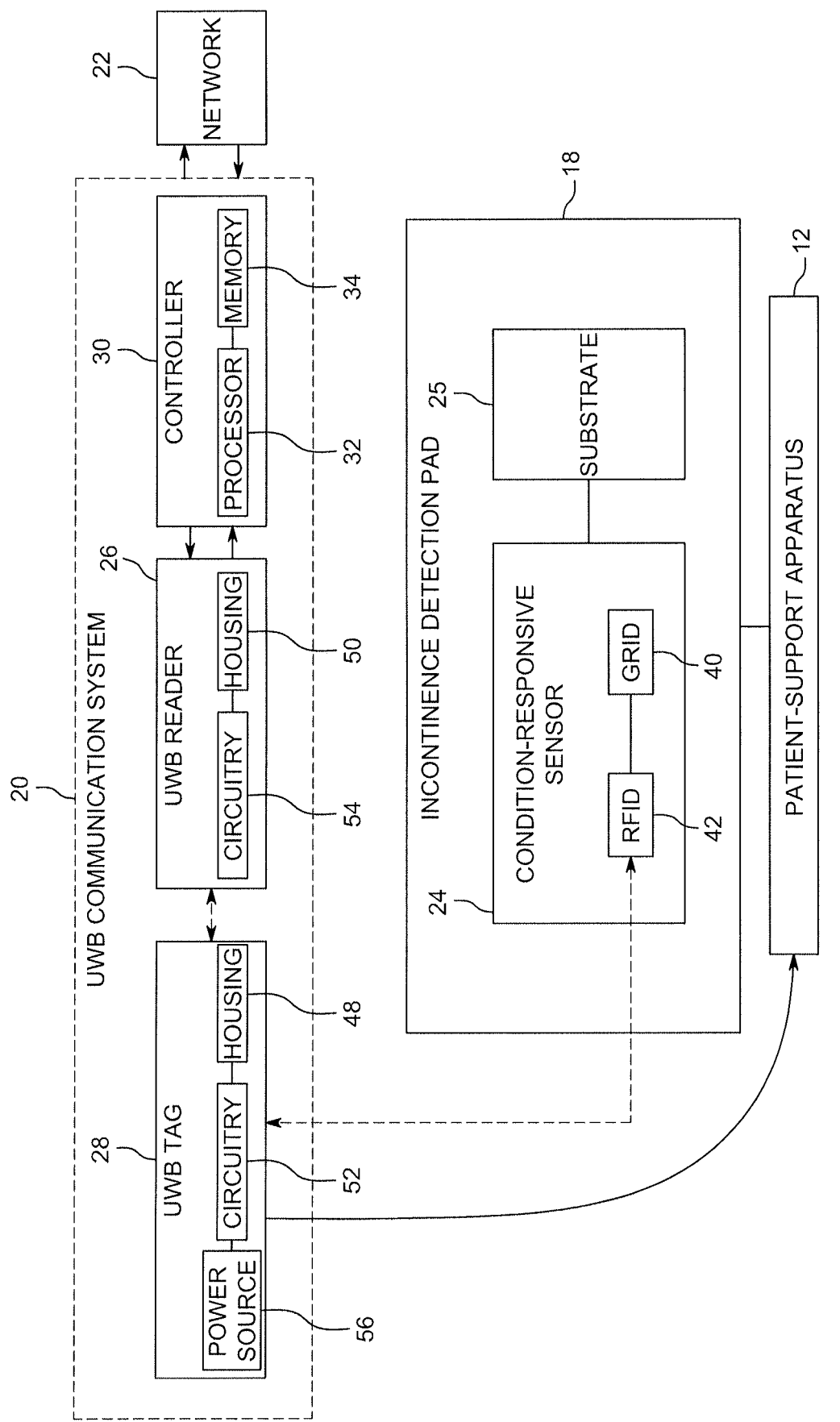
FIG. 2 is a diagrammatic view of the incontinence detection and location system of FIG. 1 including an incontinence detection pad and an ultra-wideband communication system.

The incontinence detection pad 18 includes a condition-responsive sensor 24 and a substrate 25 as shown diagrammatically in FIG. 2. The condition responsive sensor 24 is configured to provide incontinence signals in the presence of incontinence fluids to indicate that an incontinence event has occurred on the incontinence detection pad 18. The substrate 25 may include one or more absorbent layers to retain the incontinence fluid and one or more moisture-barrier layers to block the incontinence fluid from reaching the mattress 16. In the illustrative embodiment, the condition-responsive sensor 18 is integrated into the substrate 25 of the incontinence detection pad 18 between one or more of the layers forming the substrate. In another embodiment, the condition-responsive sensor 24 overlays the substrate 25 and is permeable to incontinence fluids. In each embodiment, the substrate 25 absorbs and retains fluids therein while the condition-responsive sensor 24 senses the fluids on and/or in the incontinence detection pad 18.

As shown in FIG. 1, the patient support apparatus 12 is positioned in a room with a plurality of walls. The UWB communication system 20 includes one or more ultra-wideband readers 26 coupled to the walls of the room at various locations and an ultra-wideband tag 28 coupled to the patient support apparatus 12 in communication with the condition-responsive sensor 24. The UWB tag 28 is configured to provide signals to readers 26 in proximity to the UWB tag 28 in response to the conditions sensed on the incontinence detection pad 18 by the condition-responsive sensor 24.

The condition-responsive sensor 24 may include a detection grid 40 and an RFID tag 42 coupled to the detection grid 40. The detection grid 40 has a plurality of electrically conductive traces printed on or fitted in the substrate 25 of the incontinence detection pad 18. The plurality of traces allow for an estimation of a volume of fluid on the incontinence detection pad 18. Some examples of suitable detection grids with a plurality of electrically conductive traces are shown and described in U.S. Patent Pub. Nos. 2017/0065464, U.S. Patent Pub. No. 2018/0021184, and U.S. Patent Pub. No. 2019/0060137, which are already incorporated by reference herein.

The RFID tag 42 is illustratively a passive RFID tag with an antenna and integrated circuitry. The RFID tag 42 is periodically excited by the UWB reader 26 or the UWB tag 28 and transmits an input signal associated with a sensed value across the detection grid 40. The sensed value changes depending on whether moisture is present or absent from the incontinence detection pad 18 and, hence, changes the input signal that is provided by the RFID tag 42.

Figure 6:
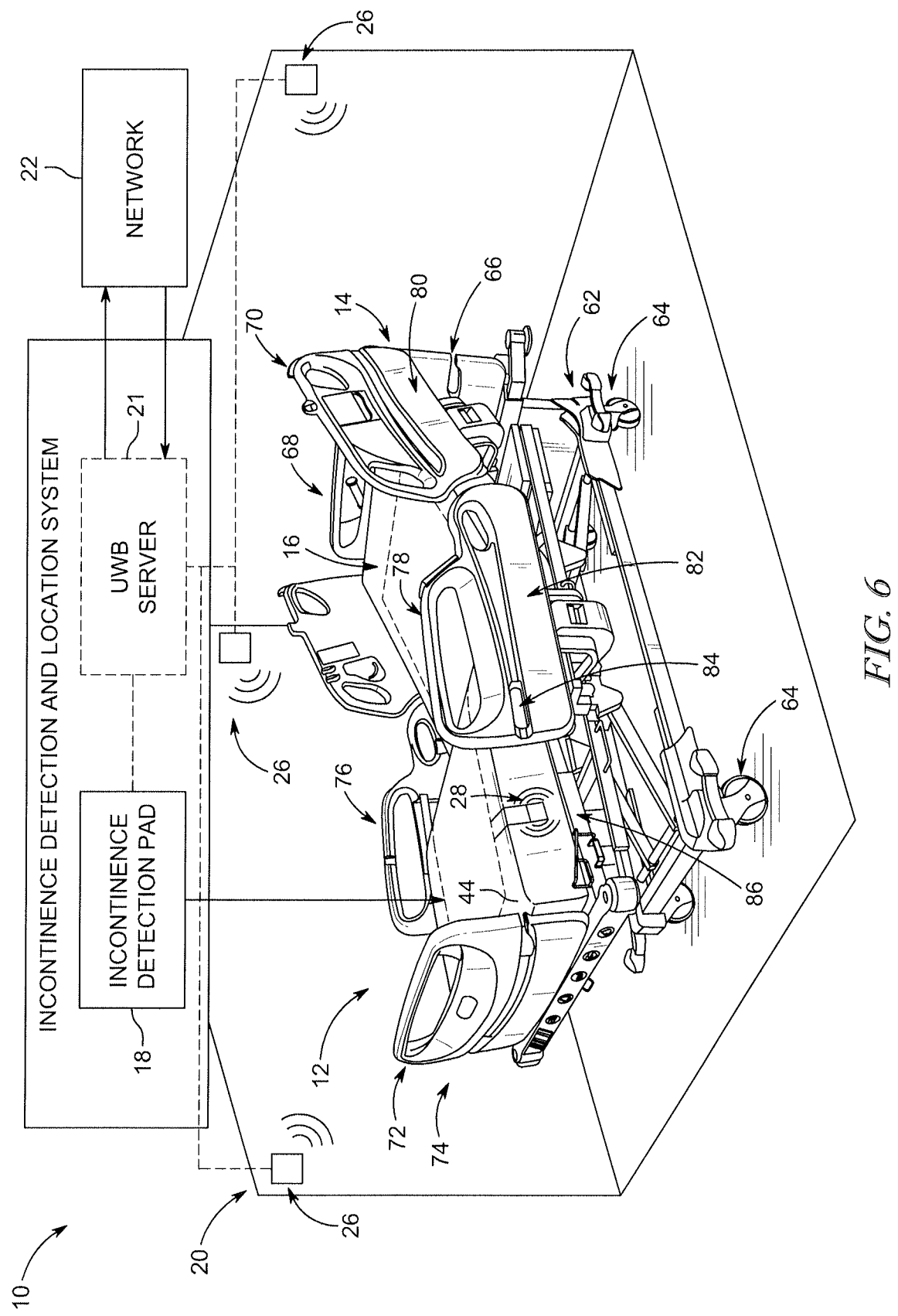
FIG. 6 is a perspective view of the patient support apparatus and another incontinence detection and notification system according to the present disclosure.
Figure 9:
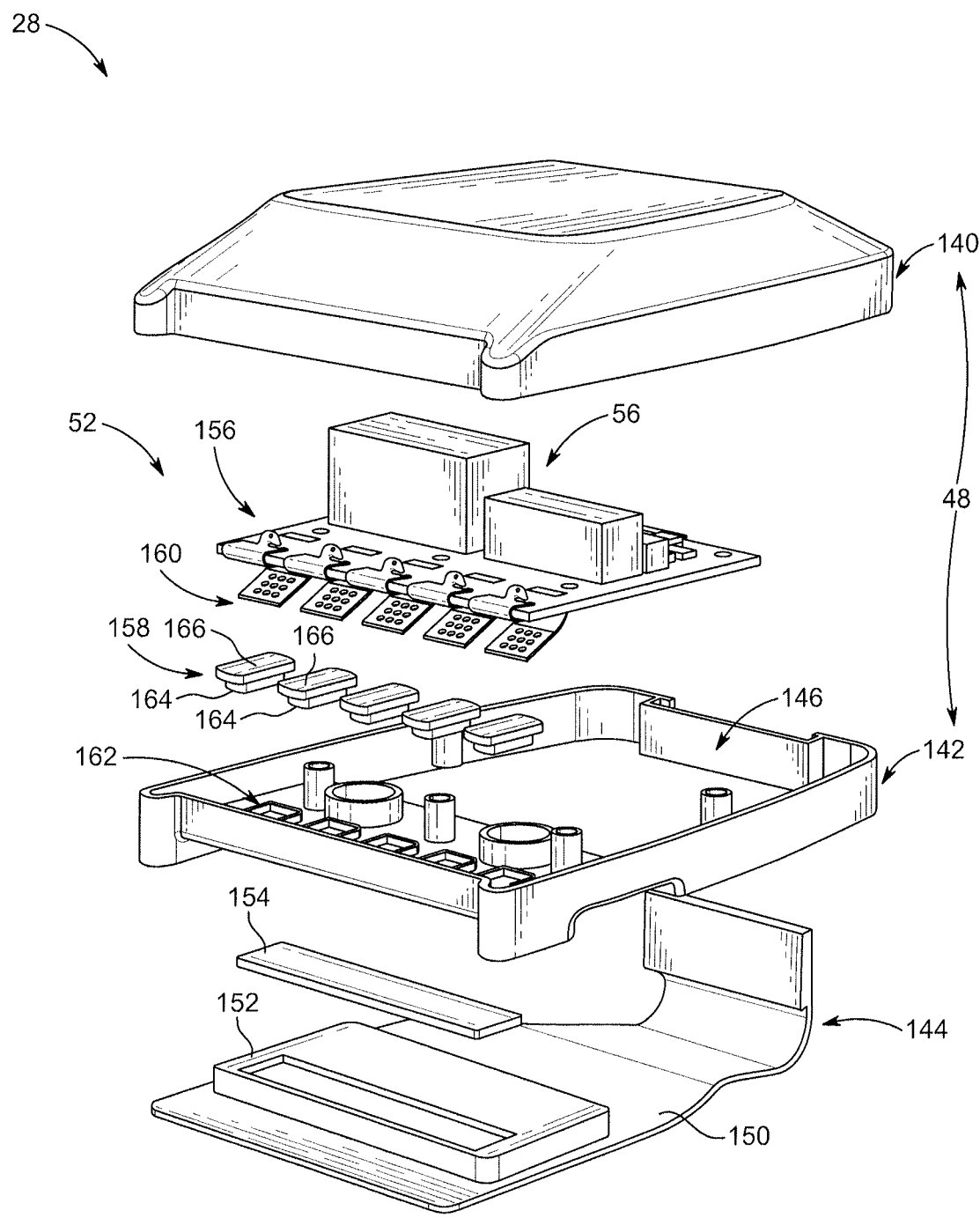
FIG. 9 is an exploded assembly view of the wireless tag.

After the patient experiences an incontinence event, the incontinence fluid is absorbed into the substrate 25 of the incontinence detection pad 18 and interconnects two or more of the electrically conductive traces of the detection grid 40. In this situation, the signal provided by the RFID tag 42 to the UWB tag 28 indicates the presence of moisture and the UWB tag 28 outputs an incontinence signal to the one or more UWB readers 26 which is processed and relayed through the UWB communication system 20 to network 22. It should be appreciated that in some embodiments the UWB tag 28 itself may be coupled to the detection grid 40 and the RFID tag 42 may be removed as shown in FIGS. 6 and 9.

In this way, the system 10 is able to detect an incontinence fluid, determine that an incontinence event has occurred, and report the incontinence event through the UWB communication system 20 to hospital caregivers, a nurse call system, or an EMR (electronic medical record) system to allow patients to be quickly removed from the soiled environment. In some embodiments, the sensor 24 communicates wirelessly with the UWB communication system 20. In other embodiments, a wired connection is provided between the sensor and the UWB communication system 20.

As shown in FIG. 1, the RFID tag 42 is a distinct flap that extends away from the incontinence detection pad 18 and hangs below a surface 44 of the mattress 16. In another embodiment the RFID tag 42 is contiguous with an outer perimeter of the incontinence detection pad 18. In both of these embodiments, the RFID tag 42 is kept out from under a patient that may lay on top of the incontinence detection pad 18 and disrupt signals to and from the RFID tag 42. The UWB tag 28 is illustratively coupled to a foot end 74 of the patient support apparatus 12 adjacent to the RFID tag 42. This arrangement increases signal strength between the UWB tag 28 and the RFID tag 42.

Figure 3:
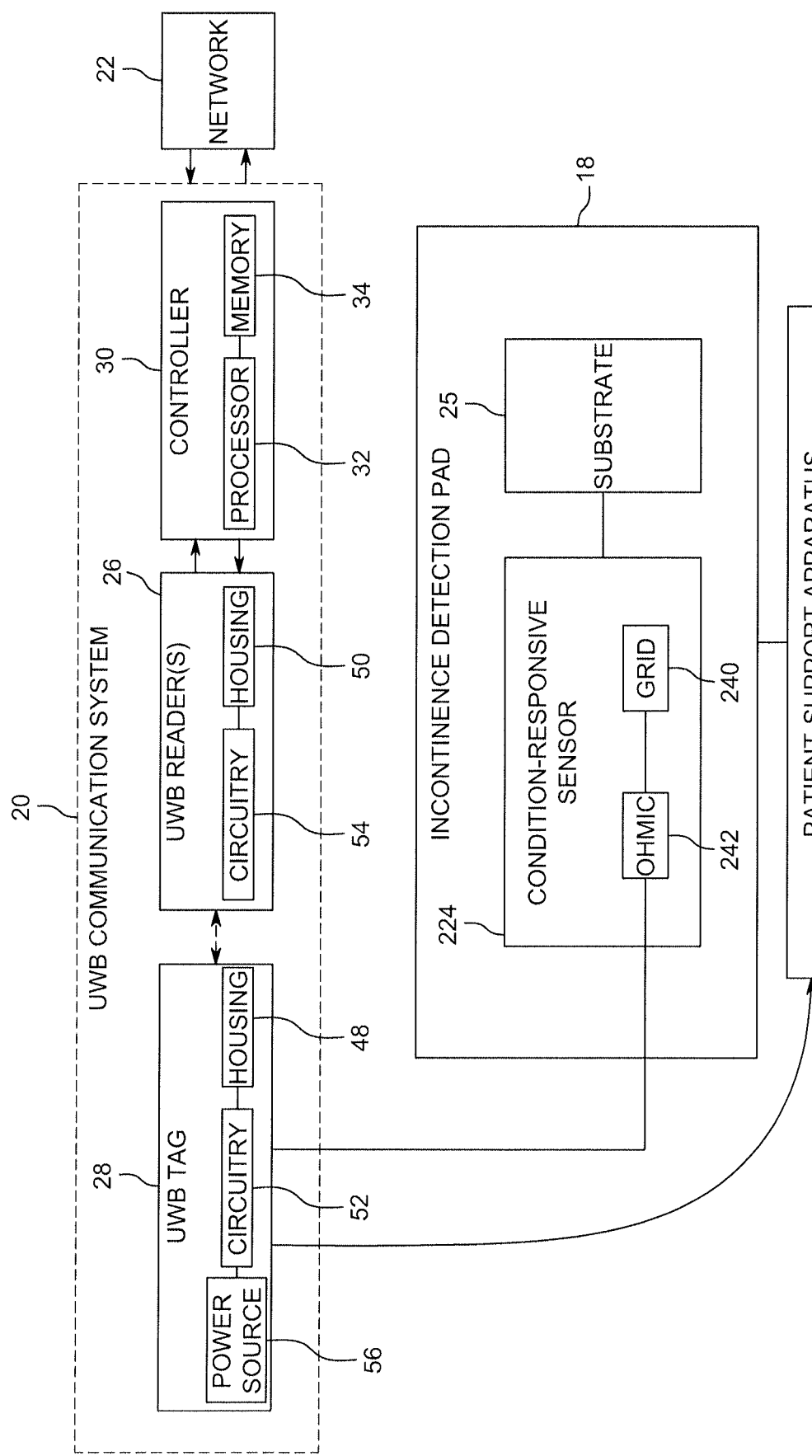
FIG. 3 is a diagrammatic view of another incontinence detection and location system similar to the system shown in FIG. 2.

Referring now to FIG. 3, another embodiment of a condition responsive sensor 224 may be used in place of condition-responsive sensor 24 shown in FIG. 2. The condition-responsive sensor 224 is similar to condition-responsive sensor 24 except condition-responsive sensor 224 includes an ohmic sensor 242 instead of RFID tag 42. The ohmic sensor 242 is coupled directly to the UWB tag 28 and a detection grid 240 with a reusable electronics package. The detection grid 240 includes a plurality of electrically conducive traces and the ohmic sensor 242 is configured to measure a resistance between each of the traces and provide a signal to the UWB tag 28 indicative of a resistive value. As moisture is introduced onto the incontinence detection pad 18 the resistive value changes. The signals transmitted by the UWB tag 28 to the UWB reader 26 also change in response to the moisture which indicates that an incontinence event has occurred.

In the illustrative embodiment, the UWB tags 28 and readers 26 also cooperate to provide a locating system, sometimes referred to as a real time locating system (RTLS) in the art, that tracks the location of the incontinence detection pad 18 throughout the healthcare facility. In the illustrative embodiment, the locating system is embodied as a high-accuracy locating system such as an ultra-wideband locating system, but this need not be the case in other embodiments of high-accuracy locating systems such as those using radio detection and ranging (RADAR) equipment or cameras and/or other imaging equipment.

The UWB communication system 20 includes the one or more UWB readers 26, the UWB tag 28, and a controller 30 as shown in FIG. 2. The controller 30 may also be referred to as a central hub computer or server for the UWB communication system 20. The controller 30 is communicatively coupled to each of the readers 26 and includes a microprocessor 32 and a memory storage device 34 coupled to the microprocessor 32. The memory storage device 34 is programmed with instructions that, when executed, allow the controller 30 to control operations of the incontinence detection and location system 10.

The UWB readers 26 receive location signals (or pings) from UWB tag 28. The location signals from the UWB tag 28 include a tag identification (ID) which is unique to each UWB tag 28 and allows the controller to determine which UWB tag 28 is providing the signals. In some embodiments, each of the UWB reader's 26 include a reader ID that correlates to particular locations in the healthcare facility. Thus, the controller 30 determines the locations of UWB tag 28 within the healthcare facility by correlating the tag ID's with the reader ID's and, ultimately, with the location correlated with the reader ID's.

According to the present disclosure, the portion of system 10 that operates as a high-accuracy locating system using UWB technology is able to determine the location of each UWB tag 28 within about one foot (30.48 cm) or less of the tag's actual location. In other embodiments, the locating system is able to determine the location of each UWB tag 28 that is in communication with at least three of UWB readers 26 within about three feet (91.44 cm) or less of the tag's actual location and such embodiments are still considered to be high-accuracy locating systems according to the present disclosure.

In the illustrative embodiment, the UWB tag 28 is configured as a UWB transceiver, and the UWB readers 26 are configured as UWB transceivers. The UWB readers 26 are stationary and the UWB tag 28 are mobile, but their circuitry otherwise may be substantially the same. Thus, UWB tag 28 and UWB readers 26 each include a housing 48, 50 that contains associated circuitry 52, 54. The circuitry 52, 54 of UWB tag 28 and UWB readers 26 includes, for example, a processor such as a microprocessor or microcontroller or the like, memory for storing software, and communications circuitry including at least one transmitter, receiver, and antenna. UWB readers 26 each include mounting hardware (not shown), such as brackets or plates or the like, in some embodiments, to permit the UWB readers 26 to be mounted at fixed locations in the patient rooms and other locations of the healthcare facility with fasteners such as screws or the like. The UWB tag 28 also includes suitable mounting hardware to permit the UWB tag 28 to be mounted to the patient support apparatus 12.

The UWB tag 28 may further include a power source 56 such as a battery as shown in FIGS. 2 and 3. The UWB tag 28 is also configured to provide battery-life signals which are relayed to the controller 30 for monitoring. The controller 30 monitors the battery-life signals and is configured to output a command signal when a battery life of the power source 56 reaches a predetermined threshold. This notifies a caregiver or a technician that the power source 56 should be replaced to avoid any disruptions in the UWB communication system 20. The battery may be recharged when the controller determines that the battery life has reached the predetermined threshold. The battery may be recharged wirelessly such as by inductive charging, radio charging, resonance charging, or any other suitable recharging method.

It should be noted that the UWB communication system 20 in the present disclosure may be referred to as an ultra-low power system. Accordingly, the power source 56 may have a battery life of at least a year, although, the battery life may change with the frequency of pings the UWB tag 28 and/or the system 10 has been designed to provide. Alternatively, the UWB tag 28 may receive power from a direct connection with the patient support apparatus 12 or another location in the room such as a wall outlet or a power bank servicing other devices in the room.

The UWB reader 26 is directly connected to the controller 30 as shown in FIG. 2. In some embodiments, the UWB readers 26 may be wirelessly connected to the controller 30 and capable of receiving and relaying data between the UWB tag 28 and the controller 30. Upon receipt of the signals from the UWB tag 28, the UWB reader 26 relays the signals to the controller 30. The controller 30 then processes the signals and provides outputs depending on the status of the incontinence detection pad 18 or other patient data signals transmitted through the UWB communication system 20. The signals provided by the UWB tag 28 include both incontinence data signals and location data signals associated with the incontinence detection pad 18. Thus, the UWB tag 28 is configured to provide means for transmitting a transmission including both the incontinence data signals and the location data signals to the UWB reader 26 simultaneously once an incontinence event occurs.

In the illustrative example, the UWB communication system 20 is also communicatively coupled to network 22 which may include various servers or computers of the healthcare facility, such as a nurse call server, an EMR server, or an admission/discharge/transfer (ADT) computer, just to name a few. Network 22 also includes the infrastructure (e.g., wireless access points, Ethernet jacks such as RJ-45 connectors, wires, routers, gateways, etc.) provided in a healthcare facility used to communicate between various computer devices and servers (e.g., personal computers, servers, laptop computers, patient care equipment, etc.) that are coupled to the infrastructure. The various subsystems described herein include components that may communicate with each other using portions of network 22. In the illustrative example, UWB readers 26 communicate with controller 30 via portions of network 22.

The outputs provided by the controller 30 may cause one or more alerts or notifications to be displayed so that a caregiver is notified that the patient has experienced an incontinence event and where the patient is located. The care giver may then timely respond to the alert or notification to address the situation. Such notification may be displayed on various devices, such as, an interface on the patient support apparatus, a monitor in the patient's room, a monitor at a nurse call station, a mobile device, or any other suitable device. In other embodiments, an audible notification may be provided.

As shown diagrammatically in FIGS. 1-4, various lines interconnect the components associated with the UWB communication system 20 and the incontinence detection pad 18. It should be appreciated that solid lines represent bidirectional communication over wired data links (including electrical wires or fiber optic data links) while dashed lines represent bidirectional communication over a wireless data link, at the discretion of the designer of the system. The UWB readers 26 communicate wirelessly with the UWB tag 28 using radio frequency (RF). It is known that RF signals are able to pass through walls, ceilings, floors, and other objects such as people and equipment. Thus, according to this disclosure, it is not required that each patient room has a UWB reader 26 located therein in those embodiments of the locating system using RF communication.

Regardless of the number of UWB readers 26 coupled to controller 30, it is contemplated by the present disclosure that, in some embodiments, controller 30 is programmed to use signals from only a subset of the plurality of UWB readers 26 to determine the location of any given locating UWB tag 28. For example, the subset may be determined based on signal strength of signals between the particular locating UWB tag 28 and the plurality of UWB readers 26. The subset may include at least three UWB readers 26 from the plurality of UWB readers 26 having highest signal strength values as compared to others of the plurality of UWB readers 26.

Figure 4:
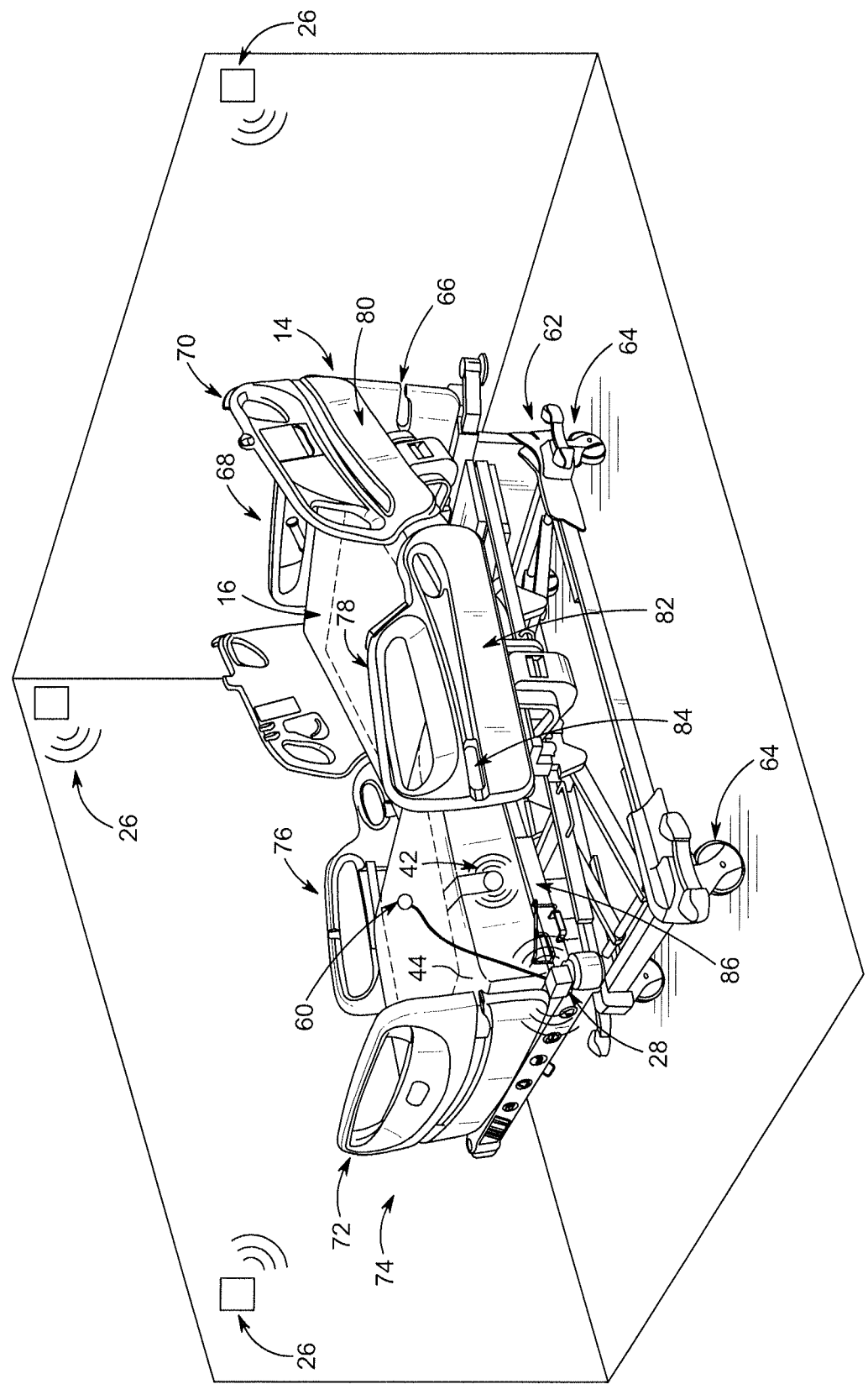
FIG. 4 is a diagrammatic view of the patient support apparatus of FIG. 1 with a patient diagnostic patch.

Although the present disclosure is directed specifically toward incontinence data signals and location data signals, the UWB tag 28 may also provide means for transmitting any patient data signals or patient support apparatus signals to the UWB reader 26. For example, as shown in FIG. 4, a patient diagnostic patch 60 is provided and may be coupled to a patient to measure various vital signs of the patient. The patient diagnostic patch 60 may also be coupled to the UWB tag 28 by a wired or wireless connection so that signals indicative of the vital signs of the patient are transmitted through the UWB communication system 20 along with the incontinence data signals and the location data signals (collectively, data signals). Such an arrangement minimizes an amount of connections from the patient and/or patient support apparatus by using only one presence through the UWB communication system 20. This arrangement can also save network traffic and may allow the UWB communication system 20 to be larger in terms of the number of nodes (i.e. patients, patient support apparatuses, rooms, buildings, etc.) and area it can cover throughout the healthcare facility. It should be appreciated that any number of devices or sensors may be coupled, wired or wirelessly, to the UWB tag 28 for transmission of their associated data signals through the UWB communication system 20.

Figure 5:
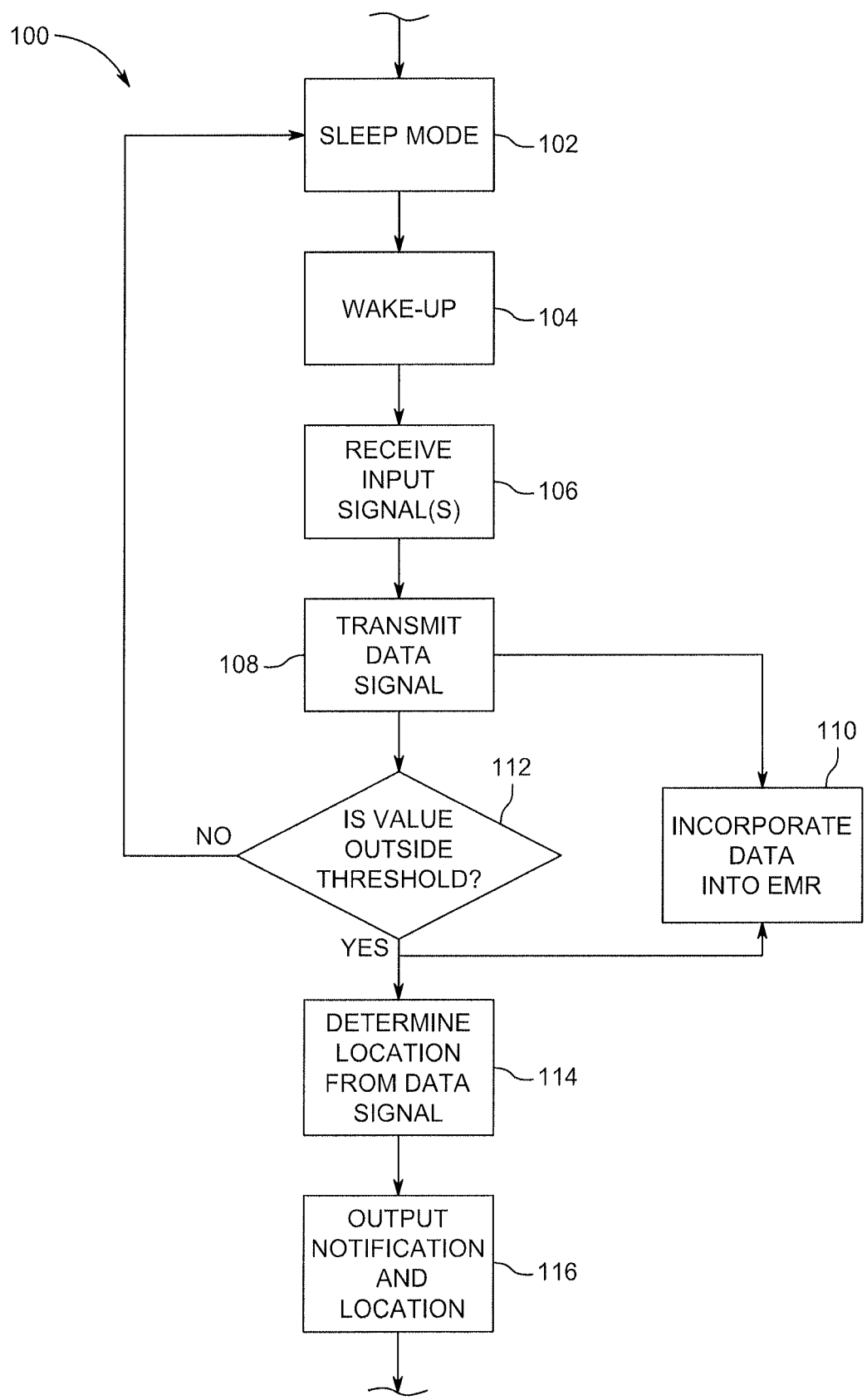
FIG. 5 is a diagrammatic flow chart of a process of analyzing data transmitted through the ultra-wideband communication system.

Referring now to FIG. 5, the controller 30 is configured to process the signals and output one or more command signals in response to the signals from the UWB tag 28 according to a process 100. The process begins at step 102 where the UWB tag 28 is kept in a deep-sleep mode to conserve power. The UWB tag 28 is configured to wake-up at step 104 to communicate with the UWB reader 26 and/or the RFID tag 42. In some embodiments, the UWB tag 28 receives periodic signals from transmitter circuitry of one or more of the UWB readers 26 and, in response, is awoken to provide the data signals to at least one of the UWB readers 26. Such an arrangement preserves battery life of UWB tag 28 because in some embodiments transmissions of tag ID's are only made by the UWB tag 28 when in communicative proximity of one or more UWB readers 26 and after receiving a request signal from at least one of the UWB readers 26.

In other embodiments, UWB tag 28 includes associated circuitry with preprogrammed instructions to wake up periodically on its own and transmit the data signals. In one example, the UWB tag 28 may be woken up twice every minute, however any suitable interval may be used at the discretion of the system designer. In still other embodiments, short range wireless beacons or infrared transmitters are mounted at fixed locations throughout the healthcare facility and send a signal with a location ID to the UWB tag 28 when it is in the vicinity of the short range beacons and, in response to receipt of the signal, the UWB tag 28 is awoken and transmits the data signals to the UWB readers 26. In each of these embodiments, one or more UWB readers 26 relay the signals to the controller 30 along with the received tag ID of the UWB tag 28, a respective reader(s) ID and, if applicable, the location ID.

Once the UWB tag 28 is awake, the UWB tag 28 receives an input signal from the condition-responsive sensor 24, 224 at step 106. The input signal in the illustrative embodiment is indicative of a resistive value between the plurality of traces included in the detection grid 40. In other embodiments, other electrical values may be measured such as voltage or amperes. The input signal changes depending on the presence or lack of an incontinence fluid on the incontinence detection pad 18. At step 106, the UWB tag 28 may also be configured to receive other input signals from other devices or sensors (i.e. patient diagnostic patch 60) coupled to the patient support apparatus or the patient as previously described.

At a step 108, the UWB tag 28 receives all of the input signals and outputs a data signal to the UWB reader containing all of the information received from the input signals in the previous step 106. The UWB reader 26 relays the data signal to the controller 30 where the information in the data signal is analyzed. All of the data analyzed by the controller 30 may be output to the network 22 for incorporation in the patient's electronic medical record (EMR) at step 110. In the illustrative embodiment, the controller 30 is configured to determine if the value associated with the incontinence data is outside of a threshold value at step 112. This would indicate that an incontinence event has occurred. If the value associate with the incontinence data is not outside of the threshold (i.e. no incontinence event has occurred) the UWB tag 28 is instructed to return to sleep mode at step 102. In another embodiment, the UWB tag 28 automatically returns to sleep mode after transmitting the data signal to the UWB reader 26 without any further input from the controller 30.

If an incontinence event has occurred, the controller 30 is configured to determine the location of the incontinence detection pad 18 from the data signal at step 114. The incontinence event is also uploaded into the patient's EMR through the network 22. Various data associated with the incontinence event may also be uploaded into the patient's EMR such as an estimation of the volume of incontinence fluid as determined by the controller 30 based on the information in the data signal. The controller 30 is then configured to output a notification through the network 22 to indicate to a caregiver that the patient has experienced an incontinence event and to indicate the location of the incontinence detection pad 18 at step 116.

Referring once again to FIG. 1, patient support apparatus 12 has a bed frame 14 which includes a base frame 62 with casters 64 and an upper frame or patient support platform 66. The patient support apparatus 12 further includes a headboard 68 at a head end 70, a footboard 72 at a foot end 74, and side rails 76, 78 coupled to the patient support platform 66. A surface or mattress 16 is supported on the patient support platform 66 and, in some embodiments, includes a plurality of inflatable support bladders as is well known in the art. Mattress 14 has an upper surface 44 on which a patient lies. Additionally, the patient support platform 66 includes a number of mattress support sections that support the mattress 14. The mattress support sections include a head section 80, a seat section 82, a thigh section 84, and a foot section 86. The head section 80, the thigh section 84, and the foot section 86 are movable relative to the seat section 82 which, in some embodiments, is affixed to upper frame members of the patient support platform 66. For example, the head section 80 may be pivotally raised and lowered relative to the seat section 82, the thigh section 84 may be pivotally raised and lowered relative to the seat section 82, and the foot section 86 may be pivotally raised and lowered relative to the thigh section 84 and the seat section 82.

Referring now to FIG. 6, the UWB tag 28 is shown being attached directly to the incontinence detection pad 18 and the RFID tag 42 has been removed. The UWB tag 28 is coupled to the detection grid 40 of the incontinence detection pad 18 and is configured to communicate wirelessly with UWB readers 26. The UWB tag 28 is configured to output a transmission to the UWB readers 26 that includes one or both of incontinence data and location data. The data received by the UWB readers 26 is then relayed to a UWB server 21 included in the UWB communication system 20. The data may then be routed to a network 22, such as a nurse call system and/or a patient's EMR.

In the illustrative embodiment shown in FIG. 6 each of the UWB readers 26 is coupled to the UWB server 21 by a wired connection, however wireless communication of data from the UWB readers 26 to the UWB server 21 is also possible. Each UWB reader 26 is coupled to the UWB server 21 by a RS-422 connector, however any suitable connector may be used such as a USB-A, USB-C, VGA, Ethernet, HDMI, etc. In the illustrative embodiment shown in FIG. 6, the UWB server 21 is connected to the network 22 by a wired connection, however wireless communication of data from the UWB server 21 to the network 22 is also possible. The UWB server 21 is coupled to the network 22 by a Ethernet connector, however any suitable connector may be used such as a USB-A, USB-C, VGA, HDMI, etc.

In one embodiment, the UWB tag 28 is configured to determine an electrical voltage, resistance, capacitance and/or current (i.e. an electrical characteristic) through the detection grid 40 and emit a signal associated with the electrical voltage, resistance, capacitance and/or current. The UWB tag 28 may provide a pulsed electrical current through the detection grid 40 at periodic intervals to sense when an incontinence event has occurred. The pulsed intervals may occur once every thirty seconds, however, any suitable time interval may be used. The UWB tag 28 may also output a status signal to the UWB readers 26 in predetermined intervals to notify the system 20 that the incontinence pad 18 is still attached and dry, that the UWB tag 28 is still monitoring for incontinence events, and/or a battery charge level of the UWB tag 28, for example. The intervals used for the status signals may be larger than the intervals used to sense for the incontinence event to increase a battery life of the UWB tag 28.

Referring now to FIGS. 7-11, an exemplary UWB tag 28 is shown as being a clip-on UWB tag 28 that may be attached removably to the incontinence detection pad 18. The UWB tag 28 shown in FIGS. 7-11 includes housing 48, circuitry 52, and power source 56. The housing 48 includes an upper shell 140, a lower shell 142, and an attachment lever 144. The upper shell 140 and the lower shell 142 define an interior space 146 that houses the circuitry 52 and the power source 56 as shown in FIG. 9. When combined, the upper shell 140 and the lower shell 142 provide a fluid-tight housing 48 for the circuitry 52 and the power source 56 so that the UWB tag 28 can be cleaned and reused.

The attachment lever 144 is coupled to at least one of the upper shell 140 and the lower shell 142 as shown in FIGS. 7-9. The attachment lever 144 is elastically deformable relative to the upper and lower shells 140, 142 between an opened position, as shown in FIG. 8, and a closed position, as shown in FIG. 7. Flexing the attachment lever 144 increases a space 148 between the lower shell 142 and the attachment lever 144 so that the UWB tag 28 can be positioned on the incontinence detection pad 18. The attachment lever 144 is formed such that it returns to a closed position after being deformed. In some embodiments, the attachment lever 144 may be attached to the upper shell 140 or the lower shell 142 with a hinged connection such that the attachment lever 144 pivots about an axis relative to the upper and lower shells 140, 142.

The attachment lever 144 includes a flexible flange 150, an attachment rib 152, and an attachment magnet 154 as shown in FIG. 9. The flexible flange 150 is coupled to one of the upper shell 140 and lower shell 142 to locate the attachment lever 144 relative to the upper shell 140 and the lower shell 142. The attachment rib 152 protrudes away from the flexible flange 150 into the space 148 to increase grip on the incontinence detection pad 18. The attachment magnet 154 is coupled to a surface of the attachment rib 152 and is exposed to the space 148. The attachment magnet 154 is configured to interact with other portions of the UWB tag 28 to pull the attachment lever 144 toward the lower shell 142 and apply a compressive force on the incontinence detection pad 18.

The circuitry 52 includes a circuit board 156 including a microprocessor, memory and one or more transceivers, a plurality of contacts 158, and a plurality of spring clips 160 that correspond with the plurality of contacts 158 as shown in FIG. 9. The plurality of contacts 156 are positioned within respective openings 162 formed in the lower shell 142. A lower end 164 of each contact 158 is exposed to space 148 between the attachment lever 144 and the lower shell 142. An upper end of each contact 158 engages a respective spring clip 160. The plurality of spring clips 160 are mounted on the circuit board 156 to transfer electric signals from the contacts 158 to the circuit board 156. In some embodiments, the circuitry 52 processes information received from the traces included in the detection grid 40 and determines if an incontinence event has occurred. In other embodiments, the circuitry 52 relays the information sensed on the detection grid 40 to the UWB readers 26 and controller 30 for processing to determine if an incontinence event has occurred.

Figure 12:
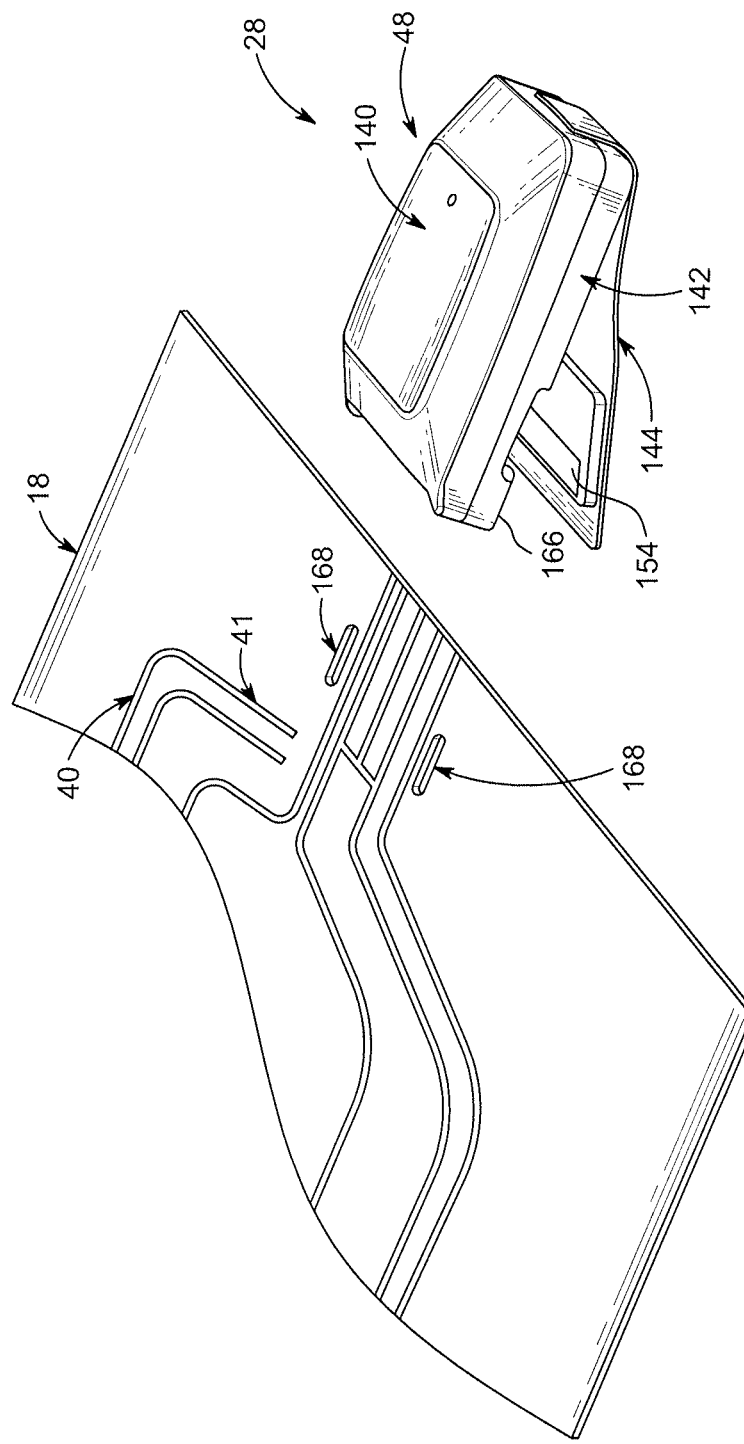
FIG. 12 is a perspective view showing the wireless tag being positioned to attach to an incontinence detection pad.

Each of the contacts 158 corresponds with an individual electrical trace 41 included in the detection grid 40 of the incontinence detection pad 18 as shown in FIGS. 9 and 12. Each of the contacts 158 is also aligned with the attachment magnet 154 to provide areas for the attachment magnet 154 to attract and apply the compressive force on the incontinence detection pad 18 to help maintain engagement of the contacts 158 and the traces 41.

Figure 13:
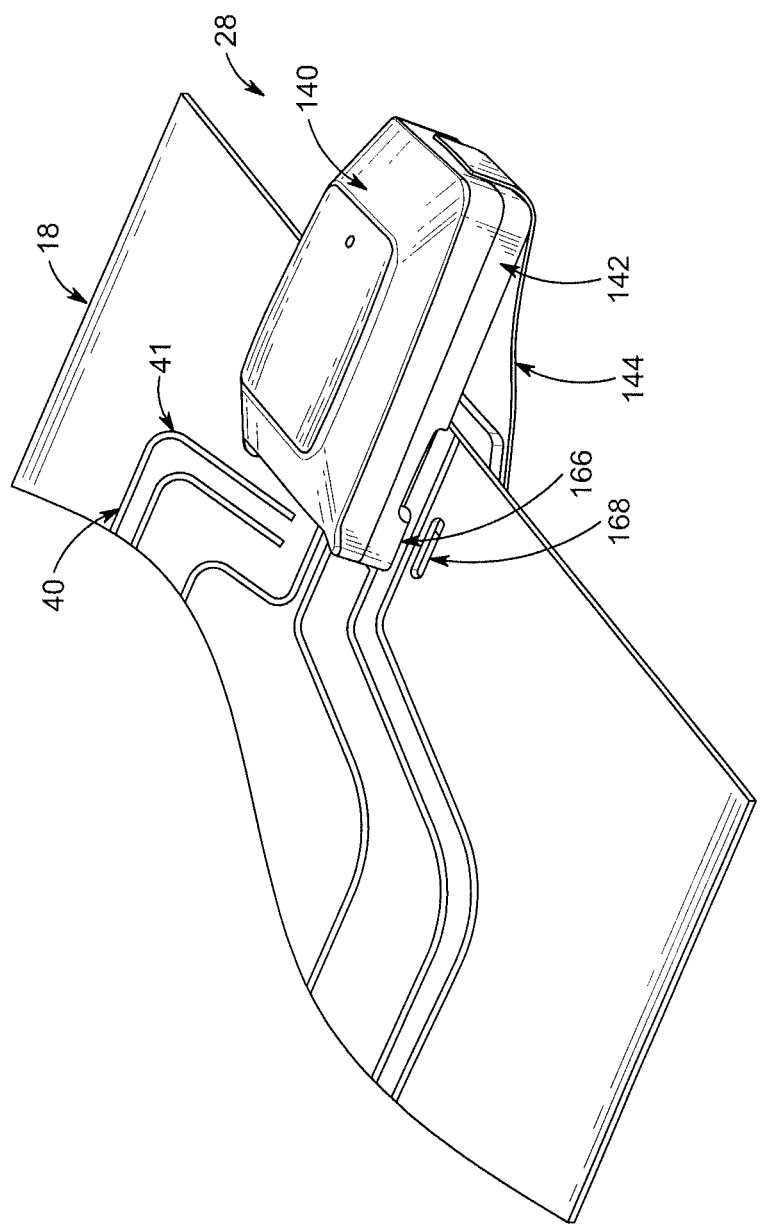
FIG. 13 is a perspective view showing the wireless tag positioned over the top of the incontinence detection pad.
Figure 14:
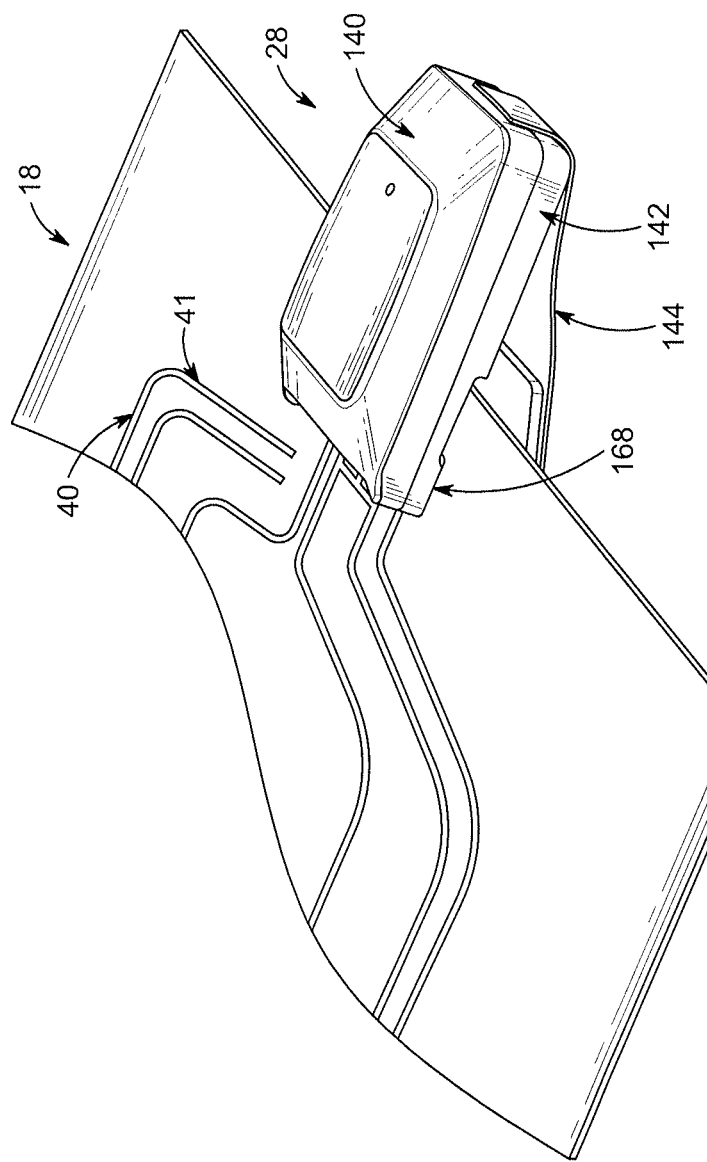
FIG. 14 is a perspective view showing the wireless tag in contact with a plurality of traces included in the incontinence detection pad.
Figure 15:
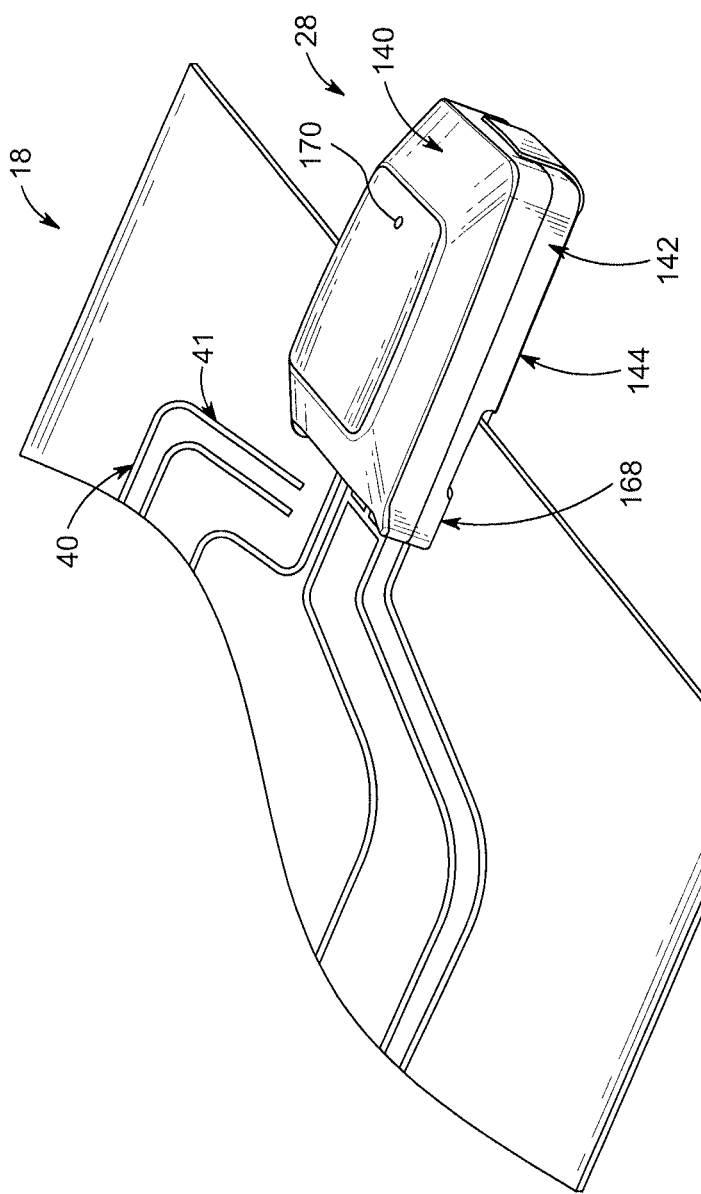
FIG. 15 is a perspective view showing the wireless tag applying a compressive force on the incontinence detection pad.

The lower shell 142 of the housing 48 includes a body 165 and a pair of index tabs 166 that extend away from the body 165 toward the attachment lever 144 as shown in FIGS. 10 and 11. The plurality of contacts 158 are positioned between the index tabs 166. The index tabs 166 correspond with a pair of index apertures 168 formed in the incontinence detection pad 18 as shown in FIGS. 12-15. To install the UWB tag 28 on the incontinence detection pad 18, a user, such as a caregiver, deforms the attachment lever 144 to the opened position as shown in FIG. 12. The incontinence detection pad 18 may then be position in the space 148 formed between the attachment lever 144 and the lower shell 142 as shown in FIG. 13. The index tabs 166 may then be aligned with and inserted into the index apertures 168 to position the contacts 158 in engagement with each trace 41 as shown in FIG. 14. The attachment lever 144 may then be released to return to the closed position so that the UWB tag 28 is attached to the incontinence detection pad 18 as shown in FIG. 15.

The UWB tag 28 may further include an indicator light 170 to indicate a status of the UWB tag 28 or of conditions sensed on the incontinence detection pad 18 as shown in FIG. 15. The indicator light 170 is coupled to the upper shell 140. In one embodiment, the indicator light 170 displays a first color (i.e. green) when the UWB tag 28 determines that the incontinence detection pad 18 is dry or that an incontinence event has not occurred. The indicator light 170 may display a second color (i.e. orange) when the UWB tag 28 determines that the incontinence detection pad 18 is wet and an incontinence event has occurred. In another embodiment, the indicator light 170 displays the first color when the power source 56 has a charge level above a predetermined amount. The indicator light 170 may display the second color when the charge level of the power source 56 is below the predetermined amount to indicate that the power source 56 should be replaced.

Figure 16:
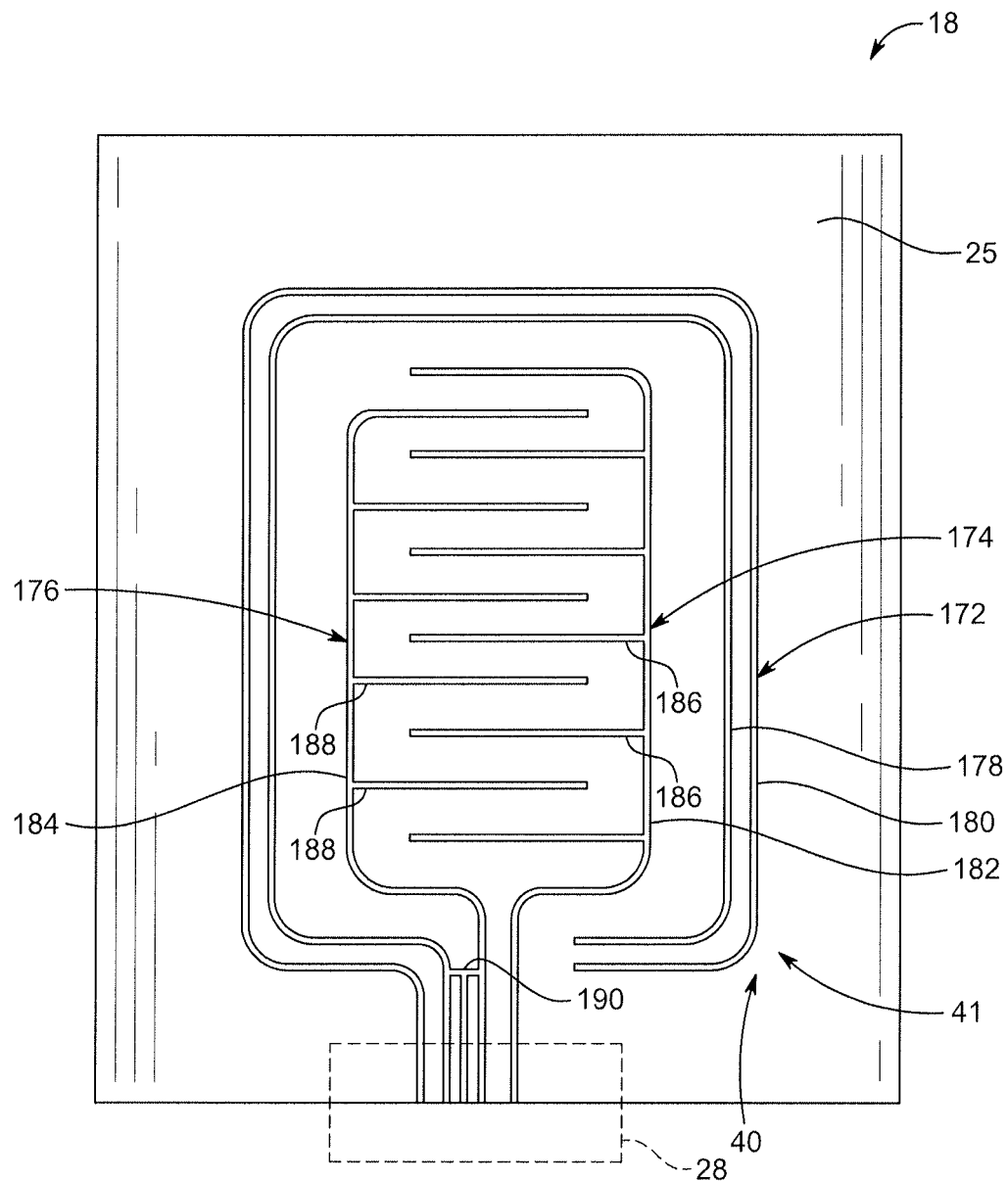
FIG. 16 is a top plane view of the incontinence detection pad.

Referring now to FIG. 16, the incontinence detection pad 18 is shown with one or more layers of the substrate 25 removed to show the arrangement of traces 41 forming detection grid 40. The traces 41 of the detection grid 40 includes a peripheral detection loop 172 and a pair of interior detection branches 174, 176. The peripheral detection loop 172 surrounds the interior detection branches 174, 176 and includes an inner trace 178 and an outer trace 180 spaced apart from one another. Each interior detection branch 174, 176 includes an arm 182, 184 and a plurality of fingers 186, 188 extending from the arm 182, 184. Each of the plurality of fingers 186, 188 extends toward the opposite arm 182, 184 that the fingers 186, 188 are connected to. Each finger 186, 188 is neighbored by fingers 186, 188 of the opposite interior detection branch 174, 176. In the illustrative embodiment shown in FIG. 16, an overall resistive value of the detection grid 40 decreases as more traces 41 are interconnected by fluid. The traces 41 also include a trace link 190 that interconnects one of the interior detection branches (i.e. 176) and inner trace 178 of the peripheral detection loop 172.

The detection grid 40 of the incontinence detection pad 18 may allow the UWB tag 28 and/or the controller 30 to determine if an incontinence event has occurred by analyzing a sensed rate of change of resistance of the detection grid 40. In some embodiments, the UWB tag 28 is configured to determine a first resistance of the detection grid at a first point in time and is configured to determine a second resistance of the detection grid at a second point in time. The circuitry of the UWB tag 28 may then compare the first resistance to the second resistance and provide incontinence signals indicating that the incontinence event has occurred only when a rate of change of the resistance of the detection grid 40 exceeds a predetermined rate of change. The UWB tag 28 may continuously sense the resistance or periodically awake and sense the resistance. In some embodiments, the UWB tag 28 may only sense the resistance and report the resistance at each point in time to an external controller where the resistance values are compared to determine the rate of change of resistance. Some non-limiting examples of external controllers include controller 30 or the circuitry of another device, like patient support apparatus 12.

The peripheral loop 172 and each interior detection branch 174, 176 provide a plurality of detection zones on the incontinence detection pad 18. These zones may allow the incontinence detection pad 18 to distinguish between non-incontinence fluids (i.e. sweat) and incontinence fluids based on the sensed rate of change of the resistance. For example, if only the inner trace 178 and the outer trace 180 of the peripheral loop 172 are interconnected by a fluid, the UWB tag 28 or controller 30 may determine that an incontinence event has not occurred because only a small amount of fluid is on the incontinence detection pad 18 and/or near an outer edge of the pad 18. If multiple fingers 186, 188 are interconnected by fluid, the UWB tag 28 or controller 30 may determine that an incontinence event has occurred due to the sudden presence of a large amount of fluid in a generally central area of the detection grid 40. If the fingers 186, 188 and the peripheral loop 172 are interconnected by fluid, the UWB tag 28 or the controller 30 may determine that an excessive incontinence event has occurred and that the fluid may have reached the patient's bed sheets, which should now be changed. A separate and different alert may be sent to the nurse call station for each of these examples and for other examples which the detection grid 40 may allow to be sensed.

It should be noted that although the system 20 is described herein as a UWB communication system 20, any suitable wireless means may be used to communicate data signals such as Bluetooth, Bluetooth LE, Zigbee, WIFI, or a custom wireless protocol, for example. Such systems may not include UWB readers 26, UWB tag 28, or controller 30. Instead, such systems may include a wireless tag that is configured to communicate with a device that has its own connection to the network 22 or a nurse call system, such as patient support apparatus 12. Two illustrative examples of a system with this configuration are described below with reference to FIGS. 17 and 18.

Figure 17:
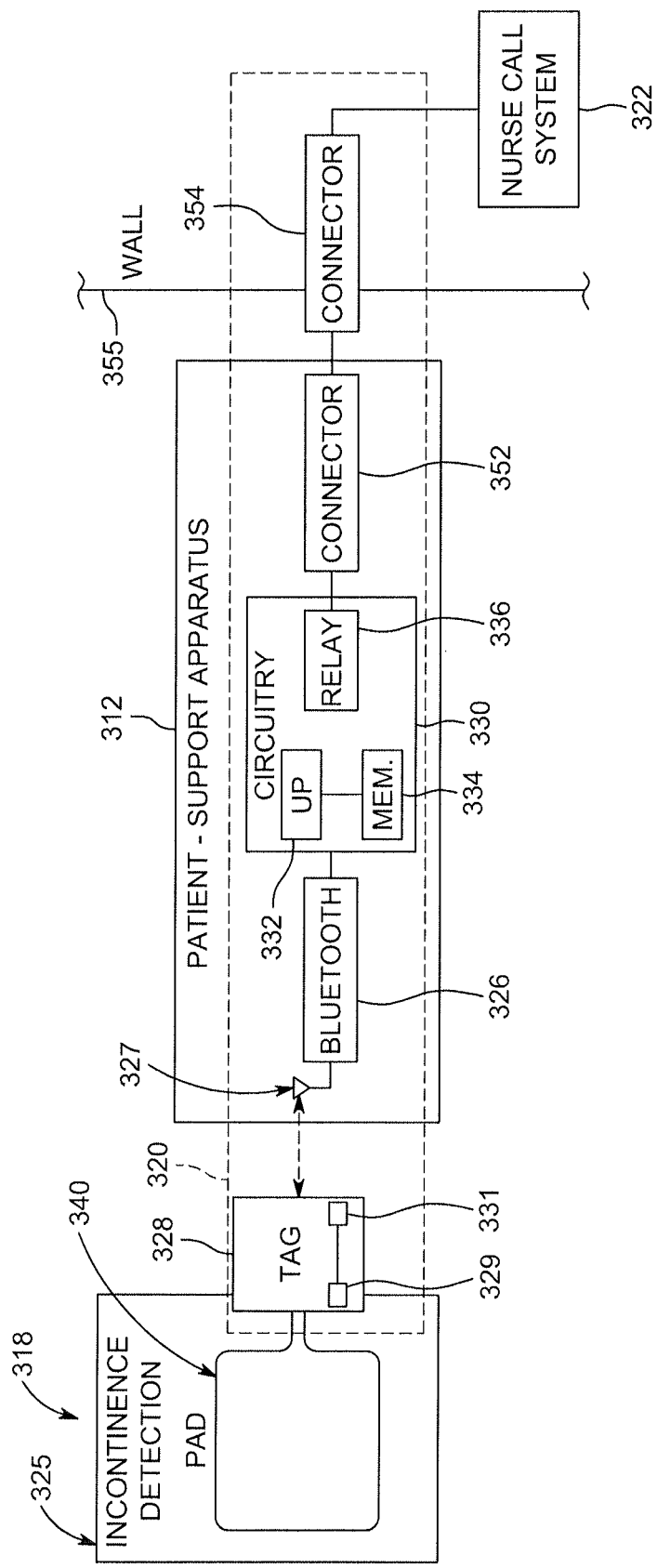
FIG. 17 is a diagrammatic view of another embodiment of an incontinence detection system.

Referring now to FIG. 17, an incontinence detection system 300 includes an incontinence detection pad 318 and a communication system 320. The incontinence detection pad 318 is configured to rest on the mattress 16 shown in FIGS. 1 and 4 in the illustrative embodiment. The communication system 320 is communicatively coupled to the incontinence detection pad 318 and is configured to transfer data between the incontinence detection pad 318 and a patient support apparatus 312 which is then relayed to a network 322, such as a nurse call system.

The incontinence detection pad 318 includes a substrate 325 that absorbs incontinence fluid and a detection grid 340 coupled to the substrate 325. The substrate 325 is substantially similar to substrates 25, 225 described above. The detection grid 340 is substantially similar to detection grids 40, 240 described above.

The communication system 320 includes a Bluetooth module 326 coupled to the patient-support apparatus 312 and in wireless communication with a wireless tag 328 coupled to the incontinence detection pad 318. The tag 328 communicates wirelessly with circuitry 330 included in the patient-support apparatus 312 as shown in FIG. 17. In particular, the Bluetooth module 326 is coupled to the circuitry 330 and includes an antenna 327 to receive and relay signals from the tag 328 to the circuitry 330. Although the Bluetooth module 326 and the wireless tag 328 communicate using Bluetooth signals, it should be appreciated that any type of signal may be used. The wireless tag 328 may be a clip-on tag such as UWB tag 28 described above.

The wireless tag 328 is coupled to the detection grid 340 and is configured to output signals in response to conditions (i.e. the presence of moisture) present on the incontinence detection pad 318. The signals output from the wireless tag 328 are received by the antenna 327 of the Bluetooth module 326. In some embodiments, the circuitry 330 includes a microprocessor 332 and memory 334 and is configured to process the signals to determine if an incontinence event has occurred. The circuitry 330 also includes a relay or switch 336 that closes if the signals indicate that an incontinence event has occurred. With the relay 336 closed, an incontinence event signal is provided to a nurse call system 322. In the illustrative embodiment, the incontinence event signal is transferred through a wired connection including a first connector 352 coupled to the patient support apparatus 12 and a second connector 354 coupled to a wall 355. From the second connector 354 the incontinence event signal is transferred to the nurse call system 322. The circuitry 330 of the patient support apparatus 312 may also include location data that is transmitted with the incontinence event signal. Thus, incontinence detection system 300 is configured to detect an incontinence event and determine the location of the incontinence event.

In another embodiment, the wireless tag 328 includes its own microprocessor 329 and memory 331 and determines whether an incontinence event has occurred on its own.

Once an incontinence event is determined to have occurred, a signal indicating the event is communicated to the Bluetooth module 326 and routed to the nurse call system 322 as described above.

Figure 18:
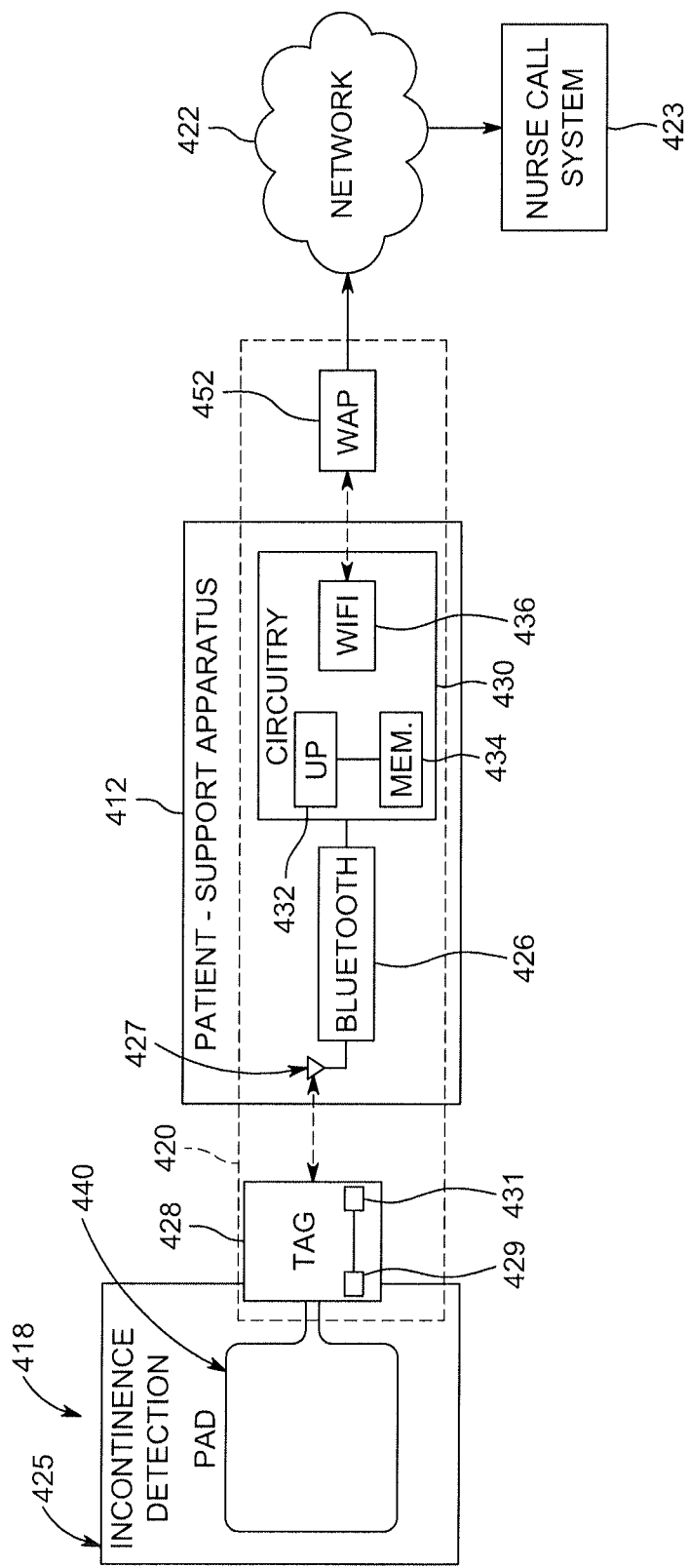
FIG. 18 is a diagrammatic view of another embodiment of an incontinence detection system.

Referring now to FIG. 18, an incontinence detection system 400 includes an incontinence detection pad 418 and a communication system 420. The incontinence detection pad 418 is configured to rest on the mattress 16 shown in FIGS. 1 and 4 in the illustrative embodiment. The communication system 420 is communicatively coupled to the incontinence detection pad 418 and is configured to transfer data between the incontinence detection pad 418 and a patient support apparatus 412 which is then relayed to a network 422 or a nurse call system 423.

The incontinence detection pad 418 includes a substrate 425 that absorbs incontinence fluid and a detection grid 440 coupled to the substrate 425. The substrate 425 is substantially similar to substrates 25, 225 described above. The detection grid 440 is substantially similar to detection grids 40, 240 described above.

The communication system 420 includes a Bluetooth module 426 coupled to the patient-support apparatus 412 and in wireless communication with a wireless tag 428 coupled to the incontinence detection pad 418. The tag 428 communicates wirelessly with circuitry 430 included in the patient-support apparatus 412 as shown in FIG. 18. In particular, the Bluetooth module 426 is coupled to the circuitry 430 and includes an antenna 427 to receive and relay signals from the tag 428 to the circuitry 330. Although the Bluetooth module 426 and the wireless tag 428 communicate using Bluetooth signals, it should be appreciated that any type of signal may be used. The wireless tag 428 may be a clip-on tag such as UWB tag 28 described above.

The wireless tag 428 is coupled to the detection grid 440 and is configured to output signals in response to conditions (i.e. the presence of moisture) present on the incontinence detection pad 418. The signals output from the wireless tag 428 are received by the antenna 427 of the Bluetooth module 426. In some embodiments, the circuitry 330 includes a microprocessor 432 and memory 434 and is configured to process the signals to determine if an incontinence event has occurred. The circuitry 430 also includes a WIFI module 436 that outputs an incontinence event signal wirelessly to a wireless access point (WAP) 452 which is then routed to a nurse call system 423 through network 422. The circuitry 430 of the patient support apparatus 412 may also include location data that is transmitted with the incontinence event signal. Thus, incontinence detection system 400 is configured to detect an incontinence event and determine the location of the incontinence event.

In another embodiment, the wireless tag 428 includes its own microprocessor 429 and memory 431 and determines whether an incontinence event has occurred on its own. Once an incontinence event is determined to have occurred, a signal indicating the event is communicated to the Bluetooth module 426 and routed to the nurse call system 432 as described above.

The system 10, 200, 300, 400 disclosed herein may lower the cost of the disposable pad 18, 218, 318, 418 by eliminating the RFID tag 42. In absence of a UWB communication link to transmit incontinence information wirelessly, another means of communicating the status of the incontinence pad may be provided. The wired incontinence detector or tag 28, 328, 428 may be battery powered by a primary lithium battery which may or may not be replaceable or rechargeable.

For incontinence detection, patient sweating may be distinguished from an incontinence event. In some embodiments, excessive patient sweating can sometimes look very similar to an incontinence event (i.e. if there is a fixed threshold for determining an incontinence event and discerning a wet or dry pad). One way to distinguish between patient sweating and an incontinence event is to look at the time rate of change of sensed resistance in detection grid 40 to determine whether there is a sudden application of a conductive, incontinence biofluid or whether the deposition of the biofluid is sweat which may have a lower time rate of change compared to the incontinence biofluid. Sweat is also conductive and in sufficient quantity, may be difficult to distinguish if only looking at a single snapshot in time of the sensed resistance of the incontinence grid.

In some embodiments, in order to convey information that an incontinence event has occurred, or the sensed resistance value between incontinence detection traces, it may be advantageous to have a low power communications channel available between the remote sensing device and the nurse-call connected medical device (i.e. a hospital bed 12, 312, 412). There are several communication protocols available which will support this communications channel and allow the conservation of energy by virtue of their low power transmission characteristics. These protocols include but are not limited to BlueTooth (i.e. Bluetooth module 326, 426), BlueTooth LE, Zigbee, UWB, or a custom wireless protocol specifically designed to minimize the power required to transmit the required data.

In some embodiments, with the wireless data connection in place, it is possible to have the wall-powered device (i.e. a hospital bed) assert a wired nurse call relay closure or circuit closure upon detection of an incontinence event which is conveyed across the low power wireless link. If it is desired to transmit the raw resistance data from the sensor instead of actually conveying over the wireless connection the incontinence event, determination of an incontinence event can be determined by the electronics on the hospital bed 12, 312, 412 which can then assert a wired nurse call signal to a nurse call station 22, 322, 422 to indicate that an incontinence event has occurred. Alternately, the calculation and determination of an incontinence event can be accomplished on the incontinence sensor and communicated over the wireless link without any intervention of the remote medical device (bed, typically) for the assertion of the nurse call output to flag the incontinence event. In some embodiments, the incontinence event is determined based on measurement of the time rate of change of the sensed pad resistance.

The following are non-limiting objectives provided by the present disclosure: Low power wireless link for conveying either incontinence event occurrence or incontinence grid resistance data to another medical device, typically a hospital bed; Remote calculation (at hospital bed or other medical device or network) of incontinence detection threshold based on sensed resistance data conveyed across the wireless RF link; Local calculation (sensing) (on a battery powered device 28, 328, 428) of incontinence event; Low power wireless sensor 28, 328, 428 coupled with wired nurse call or other event responsive system to alert caregivers of a high priority health event such as (but not limited to) an incontinence event.

In some embodiments, the present disclosure may simultaneously achieve three goals: Provide a bed-agnostic incontinence solution which does not require expensive capital equipment installs on the hospital bed, enable the use of much less expensive incontinence pads which can essentially be printed and assembled without the RFID tag, and also reduce the manufacturing cost of the pads by removing the need for the barrier layer intended to block sweat by transforming the incontinence indication from a binary function to more of a continuous, time varying response that can be read and transmitted to indicate not just the presence of an incontinence event, but also the volume of fluid expelled by the patient. In some embodiments, a low-power locating transponder 28, 328, 428 is used. The transponder 28, 328, 428 may be an Ultra Wide Band (UWB) transceiver capable of resolving its own location to within 10 cm and enabling precise correlation to a bed in a room and a patient within a multi-patient ward.

In some embodiments, a low-power analog resistance sensing circuit which measures the resistance between one or more conductive incontinence grids 40, 172, 174, 176 on the back sheet of the incontinence pad 18, 318, 418 is used. This circuit may be utilized to measure the relative resistance between the electrodes of the detection grid 40 as a function of time to allow the differentiation of sweat vs. urinary or certain types of fecal incontinence. The detection grid 40 geometry can also help indicate either the volume or physical location of the incontinence event. For instance, one of the many incontinence detection zones present on the pad could be the periphery of the pad, indicating that the event has crossed the boundary of the pad and the patient's bedsheets may need to be changed.

Although certain illustrative embodiments have been described in detail above, variations and modifications exist within the scope and spirit of this disclosure as described and as defined in the following clauses and claims.

The invention claimed is:

1. A system for detecting and locating an incontinence event comprising
a patient support apparatus configured to support a patient thereon,
an incontinence detection pad including a substrate and an incontinence detection grid coupled to the substrate, and
a communications system including a wireless tag coupled removably to the incontinence detection pad and configured to sense one or more electrical characteristics of the detection grid, a wireless module coupled to the patient support apparatus and having an antenna to receive signals from the wireless tag including the one or more electrical characteristics sensed by the wireless tag, and circuitry coupled to the patient support apparatus configured to provide a transmission of data signals to a nurse call station including incontinence signals indicative of the occurrence of an incontinence event based on the one or more electrical characteristics,
wherein the wireless tag is a clip-on wireless tag,
wherein the wireless tag includes a housing and an attachment lever coupled to the housing, and wherein the attachment lever is moveable between an opened position in which the attachment lever is at least partially spaced from the housing, and a closed position, in which the attachment lever provides a compressive force on the incontinence detection pad, and
wherein the attachment lever includes a flexible flange such that the attachment lever is configured to deform relative to the housing from the closed position to the opened position and is normally biased toward the closed position.

2. The system of claim 1, wherein the circuitry includes a microprocessor and memory storing instructions that, when executed by the microprocessor, determines whether the incontinence event has occurred from the one or more electrical characteristics sensed by the wireless tag.

3. The system of claim 2, wherein the circuitry further includes a relay that is coupled to the nurse call station by a wired connection including a first connector coupled to the patient support apparatus and a second connector coupled to a wall located in a room where the patient support apparatus is located.

4. The system of claim 2, wherein the circuitry further includes a Wifi module coupled to the patient support apparatus and a wireless access point spaced apart from the patient support apparatus, and wherein the Wifi module is configured to wirelessly relay the data signals to the wireless access point and the wireless access point is communicatively coupled to the nurse call station.

5. The system of claim 2, wherein the wireless tag is configured to sense a first resistance of the one or more electrical characteristics of the detection grid at a first point in time and is configured to sense a second resistance of the one or more electrical characteristics of the detection grid at a second point in time, and wherein the circuitry is configured to compare the first resistance to the second resistance and provide incontinence signals indicating that the incontinence event has occurred only when a rate of change of the resistance of the detection grid exceeds a predetermined rate of change.

6. The system of claim 1, wherein wireless tag includes a microprocessor and memory storing instructions that, when executed by the microprocessor, determines whether the incontinence event has occurred from the one or more electrical characteristics sensed by the wireless tag.

7. The system of claim 6, wherein the wireless tag is configured to determine a first resistance of the one or more electrical characteristics of the detection grid at a first point in time and is configured to determine a second resistance of the one or more electrical characteristics of the detection grid at a second point in time, and wherein the wireless tag is configured to compare the first resistance to the second resistance and provide incontinence signals indicating that the incontinence event has occurred only when a rate of change of the resistance of the detection grid exceeds a predetermined rate of change.

8. The system of claim 1, wherein the attachment lever further includes an attachment rib coupled to the flexible flange and arranged to extend toward the housing and an attachment magnet coupled to the attachment rib.

9. The system of claim 1, wherein the wireless tag includes a pair of index tabs and the incontinence detection pad is formed to include a pair of index openings that each receive one of the index tabs to position the wireless tag in contact with a plurality of conductive traces included in the detection grid.

10. The system of claim 9, wherein the wireless tag further includes a plurality of conductive contacts that are spaced apart laterally from one another, each conductive contact of the plurality of conductive contacts being arranged to engage a respective conductive contact of the plurality of conductive traces.

11. The system of claim 1, wherein the wireless tag includes an indicator light configured to display a first color and a second color different than the first color, the first color being displayed prior to the incontinence event, the second color being displayed after the incontinence event.

12. The system of claim 1, wherein the wireless tag includes an indicator light configured to display a first color and a second color different than the first color, the first color being displayed when the wireless tag has a power level above a predetermined amount, the second color being displayed when the wireless tag has a power level below the predetermined amount to indicate that a power source of the wireless tag should be recharged or replaced.

13. The system of claim 1, wherein the incontinence detection pad includes a distinct flap and the wireless tag is coupled to the distinct flap.

14. The system of claim 1, wherein the wireless tag includes a power source located within an interior space defined by the housing, and circuitry located within the interior space defined by the housing, and wherein the housing is leak-tight so that the wireless tag is waterproof.

15. The system of claim 1, wherein the incontinence detection grid includes a plurality of conductive traces, the plurality of conductive traces including a peripheral loop and a pair of interior detection branches.

16. The system of claim 15, wherein the peripheral detection loop surrounds the interior detection branches and includes an inner trace and an outer trace spaced apart from the inner trace.

17. The system of claim 16, wherein each interior detection branch includes an arm and a plurality of fingers extending from the arm and each of the plurality of fingers extends toward the opposite arm that the plurality of fingers are connected to.

* * * * *